(12) United States Patent
Anderson

(10) Patent No.: US 10,758,190 B2
(45) Date of Patent: Sep. 1, 2020

(54) INTERACTIVE CARDIAC TEST DATA AND ASSOCIATED DEVICES, SYSTEMS, AND METHODS

(71) Applicant: VOLCANO CORPORATION, San Diego, CA (US)

(72) Inventor: David Anderson, Temecula, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 815 days.

(21) Appl. No.: 14/961,687

(22) Filed: Dec. 7, 2015

(65) Prior Publication Data

US 2016/0157798 A1    Jun. 9, 2016

Related U.S. Application Data

(60) Provisional application No. 62/089,125, filed on Dec. 8, 2014.

(51) Int. Cl.
*A61B 5/00* (2006.01)
*A61B 5/055* (2006.01)
(Continued)

(52) U.S. Cl.
CPC ............ *A61B 5/743* (2013.01); *A61B 5/0084* (2013.01); *A61B 5/01* (2013.01); *A61B 5/02007* (2013.01);
(Continued)

(58) Field of Classification Search
CPC ..... A61B 5/743; A61B 8/0883; A61B 5/0084;
A61B 5/02055; A61B 5/0215; A61B 5/745; A61B 5/02007; A61B 5/02158; A61B 8/0891; A61B 2034/104; A61B 2034/105; A61B 2034/107; A61B 2034/108; A61B 2090/374; A61B 2090/3762; A61B 2090/3764; A61B 2576/00; A61B 2576/023; A61B 34/10; A61B 34/25; A61B 5/0035; A61B 5/004; A61B 5/0044; A61B 5/02; A61B 5/02028; A61B 5/021;
(Continued)

(56) References Cited

U.S. PATENT DOCUMENTS 6,200,268 B1    3/2001    Vince et al.
6,381,350 B1    4/2002    Klingensmith et al.
(Continued)

FOREIGN PATENT DOCUMENTS

WO    2010001327 A1    1/2010
WO    WO 2010/058398 A2    5/2010
(Continued)

*Primary Examiner* — Amanda Lauritzen Moher

(57) ABSTRACT

Devices, systems, and methods of evaluating a vascular system of a patient, are provided. In some instances, the method includes obtaining external imaging data associated with the heart; obtaining cardiac test data associated with the heart; generating a three-dimensional graphical representation of the heart using the external imaging data and the cardiac test data; and outputting the graphical representation of the heart to a display device, wherein the graphical representation of the heart includes a graphical representation of the cardiac test data. Corresponding systems and devices are also provided.

11 Claims, 9 Drawing Sheets

(51) Int. Cl.

| | | |
|---|---|---|
| *A61B 8/00* | (2006.01) | |
| *G16H 40/63* | (2018.01) | |
| *G16H 50/50* | (2018.01) | |
| *A61B 5/01* | (2006.01) | |
| *A61B 8/08* | (2006.01) | |
| *G06F 19/00* | (2018.01) | |
| *A61B 8/12* | (2006.01) | |
| *A61B 5/0215* | (2006.01) | |
| *A61B 5/02* | (2006.01) | |
| *A61B 5/0205* | (2006.01) | |
| *A61B 6/00* | (2006.01) | |
| *A61B 6/03* | (2006.01) | |
| *A61B 34/10* | (2016.01) | |
| *A61B 5/026* | (2006.01) | |
| *A61B 90/00* | (2016.01) | |

(52) U.S. Cl.
CPC ........ *A61B 5/0215* (2013.01); *A61B 5/02055* (2013.01); *A61B 5/02158* (2013.01); *A61B 5/745* (2013.01); *A61B 8/0883* (2013.01); *A61B 8/0891* (2013.01); *A61B 8/12* (2013.01); *G06F 19/321* (2013.01); *G06F 19/3481* (2013.01); *G16H 40/63* (2018.01); *G16H 50/50* (2018.01); *A61B 5/0066* (2013.01); *A61B 5/026* (2013.01); *A61B 5/055* (2013.01); *A61B 6/03* (2013.01); *A61B 6/037* (2013.01); *A61B 6/4417* (2013.01); *A61B 6/467* (2013.01); *A61B 6/503* (2013.01); *A61B 6/504* (2013.01); *A61B 8/463* (2013.01); *A61B 8/467* (2013.01); *A61B 2034/104* (2016.02); *A61B 2034/105* (2016.02); *A61B 2034/108* (2016.02); *A61B 2090/3735* (2016.02); *A61B 2090/3782* (2016.02); *A61B 2576/023* (2013.01)

(58) Field of Classification Search
CPC ....... A61B 5/024; A61B 5/026; A61B 5/0263; A61B 5/029; A61B 5/055; A61B 5/1075; A61B 5/1118; A61B 5/22; A61B 5/4858; A61B 5/6852; A61B 5/7246; A61B 5/7275; A61B 5/7278; A61B 6/03; A61B 6/032; A61B 6/481; A61B 6/503; A61B 6/504; A61B 6/507; A61B 6/5205; A61B 6/5217; A61B 6/5229; A61B 8/02; A61B 8/04; A61B 8/06; A61B 8/065; A61B 8/481; A61B 8/5223; A61B 8/5261; A61B 2090/3735; A61B 2090/3782; A61B 5/0066; A61B 5/01; A61B 6/037; A61B 6/4417; A61B 6/467; A61B 8/12; A61B 8/463; A61B 8/467; G06F 19/00; G06F 19/321; G06F 19/3481; G06F 17/10; G06F 17/5009; G06F 17/5018; G06F 19/324; G16H 50/50; G16H 40/63; G16H 10/40; G16H 10/60; G16H 30/20; G16H 30/40; G16H 50/30; G16H 50/70; A61M 5/007; G01R 33/5601; G01R 33/5635; G01R 33/56366; G06G 7/60; G06K 2009/4666; G06K 9/00147; G06K 9/46; G06K 9/4604; G06K 9/52; G06K 9/6215; G06K 9/6267; G06K 9/6298; G06T 11/00; G06T 11/001; G06T 11/008; G06T 11/20; G06T 11/60; G06T 15/10; G06T 17/00; G06T 17/005; G06T 17/20; G06T 2200/04; G06T 2207/10012; G06T 2207/10072; G06T 2207/10081; G06T 2207/10088; G06T 2207/10104; G06T 2207/10108; G06T 2007/20036; G06T 2207/20124; G06T 2207/30048; G06T 2207/30104; G06T 2210/41; G06T 2211/404; G06T 7/0012; G06T 7/0014; G06T 7/11; G06T 7/12; G06T 7/13; G06T 7/149; G06T 7/20; G06T 7/74; G06T 2207/20036; G06T 7/60; G06T 7/62; G06T 7/70; G06T 7/73; G16B 45/00; G16B 5/00; Y02A 90/22; Y02A 90/26

See application file for complete search history.

(56) References Cited

U.S. PATENT DOCUMENTS

| | | | |
|---|---|---|---|
| 7,074,188 B2 | 7/2006 | Nair et al. | |
| 7,175,597 B2 | 2/2007 | Vince et al. | |
| 7,359,554 B2 | 4/2008 | Klingensmith et al. | |
| 7,627,156 B2 | 12/2009 | Margolis et al. | |
| 7,930,014 B2 | 4/2011 | Huennekens | |
| 7,988,633 B2 | 8/2011 | Hossack et al. | |
| 9,226,672 B2 | 1/2016 | Taylor | |
| 9,339,348 B2 | 5/2016 | Davies et al. | |
| 10,478,252 B2* | 11/2019 | Taylor | A61B 6/03 |
| 2004/0097805 A1* | 5/2004 | Verard | A61B 1/00071 600/428 |
| 2008/0221442 A1 | 9/2008 | Tolkowsky et al. | |
| 2008/0275335 A1* | 11/2008 | Zhang | A61B 6/12 600/424 |
| 2011/0116598 A1 | 5/2011 | Gotman | |
| 2012/0053918 A1 | 3/2012 | Taylor | |
| 2012/0150516 A1 | 6/2012 | Taylor | |
| 2013/0046190 A1 | 2/2013 | Davies | |
| 2014/0187920 A1 | 7/2014 | Millett | |
| 2014/0247970 A1* | 9/2014 | Taylor | A61B 5/02007 382/128 |
| 2014/0270429 A1 | 9/2014 | Nair et al. | |
| 2015/0161790 A1 | 6/2015 | Takahashi | |
| 2016/0247279 A1* | 8/2016 | Lavi | G16H 50/50 |

FOREIGN PATENT DOCUMENTS

| | | |
|---|---|---|
| WO | WO 2012/014212 A2 | 2/2012 |
| WO | 2014164992 A1 | 10/2014 |

* cited by examiner

INTERACTIVE CARDIAC TEST DATA AND ASSOCIATED DEVICES, SYSTEMS, AND METHODS

CROSS REFERENCE TO RELATED APPLICATIONS

The present application claims priority to and the benefit of the U.S. Provisional Patent Application No. 62/089,125, filed Dec. 8, 2014, which is hereby incorporated by reference in its entirety.

TECHNICAL FIELD

The present disclosure relates generally to the assessment of patient's blood vessels and heart to determine an appropriate therapeutic intervention. For example, some embodiments of the present disclosure are suited for visualizing a three-dimensional model of the heart with nuclear stress test data, such as myocardial perfusion imaging data.

BACKGROUND

Innovations in diagnosing and verifying the level of success of treatment of disease have progressed from solely external imaging processes to include internal diagnostic processes. In addition to traditional external image techniques such as X-ray, MRI, CT scans, single-photon emission computed tomography (SPECT), fluoroscopy, and angiography, small sensors may now be placed directly in the body. For example, diagnostic equipment and processes have been developed for diagnosing vasculature blockages and other vasculature disease by means of ultra-miniature sensors placed upon the distal end of a flexible elongate member such as a catheter, or a guide wire used for catheterization procedures. For example, known medical sensing techniques include intravascular ultrasound (IVUS), forward looking IVUS (FL-IVUS), fractional flow reserve (FFR) determination, Instant Wave-Free Ratio™ (iFR®) determination, a coronary flow reserve (CFR) determination, optical coherence tomography (OCT), trans-esophageal echocardiography, and image-guided therapy.

When an occluded blood vessel that requires treatment is identified, a percutaneous coronary intervention (PCI) is a therapeutic procedure that can be utilized to treat the vessel. A PCI includes angioplasty and positioning a stent across the stenosis to open the vessel. Clinicians conventionally rely on angiography and physiologic measurements of pressure and/or flow, which are not meaningfully connected, to plan a therapeutic intervention. Planning the therapeutic intervention can include selecting various parameters related to the stent, such as positioning, length, diameter, etc. While the collected external cardiac test data, intravascular imaging data, and/or physiologic data can help in planning the therapeutic intervention, their efficacy is limited by the fact they exist as separate tests. For example, clinicians are unable to easily visualize where in the blood vessel the data was collected. Further, physiologic data and external cardiac test data are not integrated in a meaningful way that would allow a clinician to assess the effect of a PCI on, e.g., blood flow to the myocardium.

Accordingly, there remains a need for improved devices, systems, and methods for assessing the severity of a blockage in a vessel and, in particular, a stenosis in a blood vessel. There also remains a need for improved devices, systems, and methods for planning a therapeutic intervention by connecting external cardiac test data, physiologic data, and/or intravascular imaging data in a way that allows clinicians to efficiently plan and evaluate the proposed therapy. Further, there remains a need for providing visual depictions of a vessel that allow a clinician to plan, evaluate, and change the proposed therapy in a manner supported by the collected data.

SUMMARY

Embodiments of the present disclosure are configured to provide a three-dimensional graphical representation of the heart to allow a doctor to effectively plan a surgical procedure known as a percutaneous coronary intervention (PCI). The three-dimensional model of the heart can integrate, e.g., angiography, pressure measurements, intravascular ultrasound (IVUS) images, and nuclear stress test data. The nuclear stress test data illustrates the amount of blood/oxygen in the heart muscle as a result of blood flow through vessels in the heart or coronary arteries. The nuclear stress test data can be used to simulate the physiologic effects of deploying a stent in the coronary artery. A doctor can efficiently plan a PCI by deploying a simulated stent in the three dimensional representation of the heart and/or vessel, and evaluating the resulting, simulated physiologic effects.

In one embodiment, a method of evaluating a vascular system of a patient is provided. The method includes obtaining external imaging data associated with the heart; obtaining cardiac test data associated with the heart; generating a three-dimensional graphical representation of the heart using the external imaging data and the cardiac test data; and outputting the graphical representation of the heart to a display device, wherein the graphical representation of the heart includes a graphical representation of the cardiac test data.

In some embodiments, obtaining external imaging data includes obtaining at least one of angiography data and computed tomography data. In some embodiments, obtaining cardiac test data includes myocardial perfusion imaging data. In some embodiments, outputting a graphical representation of the heart to a display device includes outputting the graphical representation of the heart to at least one of a touch-sensitive display device and a holographic display device. In some embodiments, the graphical representation of the cardiac test data includes at least one of a pattern, shading, or coloration representative of blood flow to the myocardium. In some embodiments, the method further includes obtaining physiology data associated with a vessel. In some embodiments, obtaining physiology data associated with the vessel includes obtaining at least one of pressure measurements, flow measurements, temperature measurements. In some embodiments, generating the three-dimensional graphical representation of the heart includes generating a three-dimensional graphical representation of a vessel; and outputting the graphical representation of the heart includes outputting the graphical representation of the vessel. In some embodiments the method further includes associating the cardiac test data and at least one of the external imaging data and the physiology data. In some embodiments, the method further includes receiving a user input to simulate a therapeutic intervention; determining a simulated effect of the therapeutic intervention on the blood flow to the myocardium using the physiology data and the cardiac test data; and outputting modified graphical representation of the heart including a graphical representation of the simulated effect. In some embodiments, receiving a user input to simulate a therapeutic intervention includes receiving a user input to simulate a percutaneous coronary intervention. In some embodiments, receiving a user input includes at least one of receiving data representative of a user touch input on a touch-sensitive display device and receiving data representation of a hand gesture obtained by an input device.

In one embodiment, a system for evaluating a vascular system of a patient is provided. The system includes a first instrument sized and shaped for introduction into a vessel of the patient; and a processing system communicatively coupled to the first instrument and a display device, the processing system configured to: receive external imaging data associated with the heart; receive cardiac test data associated with the heart; receive physiology data associated with the vessel from the first instrument; associate the cardiac test data and at least one of the external imaging data and the physiology data; generate a three-dimensional graphical representation of the heart using the external imaging data, the cardiac test data, and the physiology data; and output the graphical representation of heart to a display device, wherein the graphical representation of the heart includes a graphical representation of the cardiac test data.

In some embodiments, the external imaging data includes at least one of angiography data and computed tomography data. In some embodiments, the cardiac test data includes myocardial perfusion imaging data. In some embodiments, the system further includes the display device, the display device including at least one of a touch-sensitive display device and a holographic display device. In some embodiments, the computing device is configured to output the graphical representation of the cardiac test data including at least one of a pattern, shading, or coloration representative of blood flow to the myocardium. In some embodiments, the physiology data associated with the vessel includes at least one of pressure measurements, flow measurements, temperature measurements. In some embodiments, the computing device is configured to: generate the three-dimensional graphical representation of the heart by generating a three-dimensional graphical representation of a vessel; and output the graphical representation of the heart by outputting the graphical representation of the vessel. In some embodiments, the system further includes a second instrument sized and shaped for introduction into the vessel of the patient, wherein the computing device is configured to receive pressure measurements from the first instrument and the second instrument positioned within the vessel of the patient while the second instrument is moved longitudinally through the vessel and the first instrument remains stationary within the vessel. In some embodiments, the computing device is further configured to: receive a user input to simulate a therapeutic intervention; determine a simulated effect of the therapeutic intervention on the blood flow to the myocardium using the physiology data and the cardiac test data; and output modified graphical representation of the heart including a graphical representation of the simulated effect. In some embodiments, the therapeutic intervention includes a percutaneous coronary intervention. In some embodiments, the system further includes at least one of a touch-sensitive display configured to receive a user touch input and an input device configured to generate data representative of a hand gesture.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
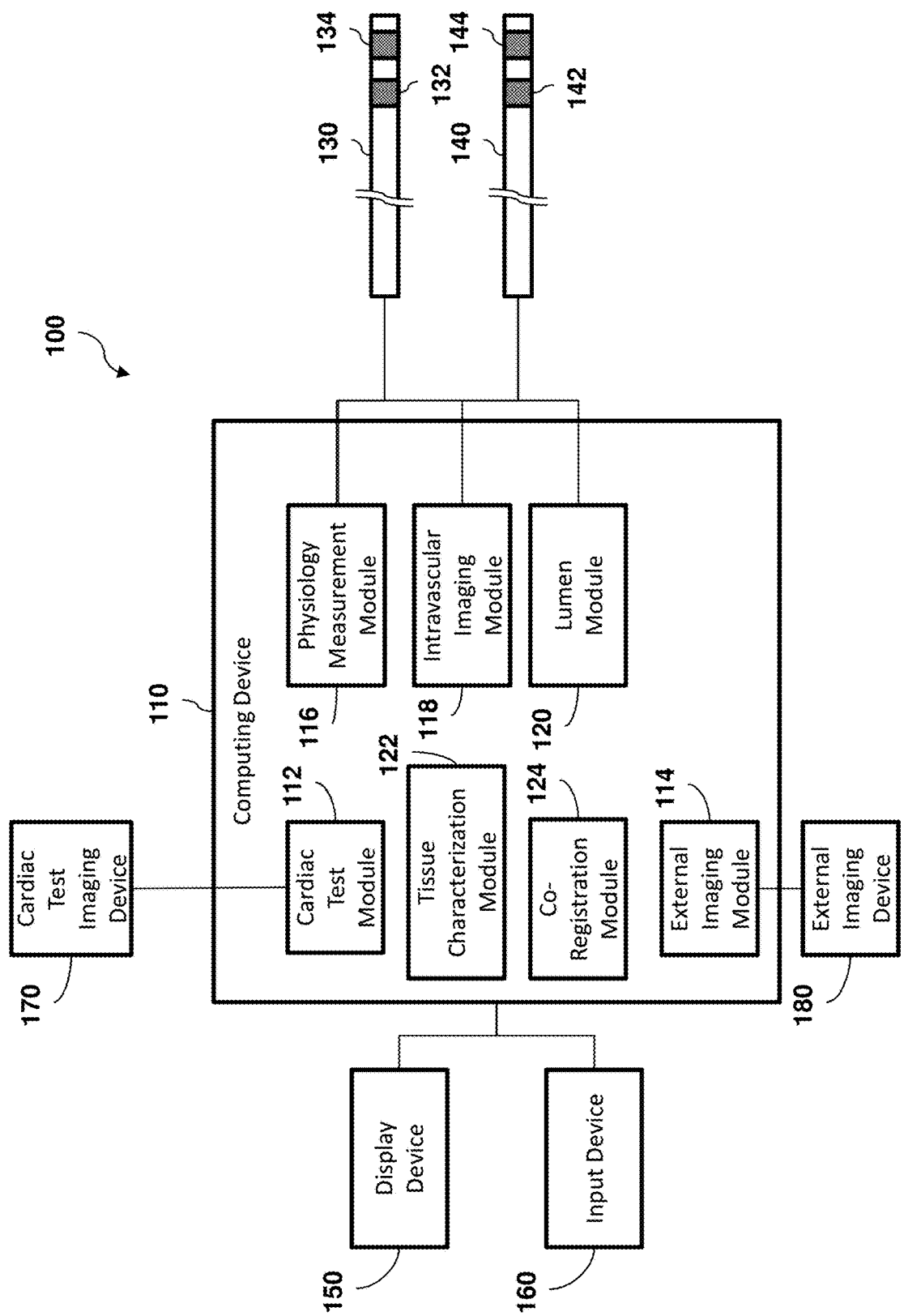
FIG. 1 is a diagrammatic, schematic view of a system according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Referring to FIG. 1, shown therein is a system 100 according to an embodiment of the present disclosure. The system 100 can be configured to assess the vasculature or the vascular system of a patient, such as to determine, plan, and/or modify a clinical response to a stenosis, blockage, or other obstruction to the flow of fluid. For example, a clinician can use the system 100 to assess the heart and/or one or more coronary arteries. The system 100 can also be used to assess various cerebrovascular vessels and/or peripheral vessels, including the legs, kidneys, aorta, brain, etc. The system 100 includes a computing device 110. The system 100 can also include one or more instruments 130 and 140.

The computing device 110 is generally representative of any device suitable for performing the processing and analysis techniques disclosed herein. In some embodiments, the computing device 110 includes a processor, random access memory, and a storage medium. In that regard, in some particular instances the computing device 110 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 110 is a console device. In some particular instances, the computing device 110 is similar to the s5™ Imaging System or the s5i® Imaging System, each available from Volcano Corporation. In some instances, the computing device 110 is portable (e.g., handheld, on a rolling cart, etc.). In some instances, all or a portion of the computing device 110 can be implemented as a bedside controller such that one or more processing steps described herein can be performed by processing component(s) of the bedside controller. An exemplary bedside controller is described in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. Further, it is understood that in some instances the computing device 110 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

In general, the instruments 130 and 140 may be any form of device, instrument, or probe sized and shaped to be positioned within a vessel. For example, the instrument 130 is generally representative of a guide wire, while instrument 140 is generally representative of a catheter. In that regard, the instrument 130 can extend through a central lumen of the instrument 140 during use within the patient's vasculature. However, in other embodiments, the instruments 130 and 140 take other forms.

The instruments 130 and 140 can include one or more sensors, transducers, and/or other monitoring elements 132, 134, 142, and 144. The elements 132, 134, 142, and 144 are configured to obtain the diagnostic information about the vessel including one or more of pressure, flow (velocity and/or volume), images (including images obtained using ultrasound (e.g., IVUS), OCT, thermal, and/or other imaging techniques), temperature, other diagnostic information, and/or combinations thereof. For example, a pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. For example, an imaging element can take the form of a rotational IVUS device, a solid-state IVUS device, an OCT device, a forward looking IVUS (FL-IVUS) device, other suitable devices, and/or combinations thereof.

While FIG. 1 illustrates that the system 100 includes two instruments 130 and 140, it is understood that the system 100 can include one or more instruments sized and shaped for introduction into the vessel of the patient. Similarly, while each instrument 130 and 140 is shown to include two monitoring elements 132 and 134, and monitoring element 142 and 144, respectively, various embodiments can include one or more monitoring elements. Various exemplary systems, instruments, sensors, transducers, and/or other monitoring elements are described in greater detail in U.S. Provisional Application No. 62/024,339, "DEVICES, SYSTEM, AND METHODS FOR IMPROVED ACCURACY MODEL OF VESSEL ANATOMY," filed Jul. 14, 2014; U.S. Provisional Application No. 62/080,023, "PERCUTANEOUS CORONARY INTERVENTION (PCI) PLANNING INTERFACE AND ASSOCIATED DEVICES, SYSTEMS, AND METHODS," filed Nov. 14, 2014; U.S. Provisional Application No. 62/089,039, "DEVICES, SYSTEMS, AND METHODS FOR VESSEL ASSESSMENT AND INTERVENTION RECOMMENDATION" filed Dec. 8, 2014; U.S. Provisional Application No. 62/090,251, "DEVICES, SYSTEMS, AND METHODS FOR IN-STENT RESTENOSIS PREDICTION" filed Dec. 10, 2014; U.S. Provisional Application No. 62/080,045, "PERCUTANEOUS CORONARY INTERVENTION PLANNING (PCI) PLANNING INTERFACE WITH PRESSURE DATA AND VESSEL DATA AND ASSOCIATED DEVICES, SYSTEMS, AND METHODS," filed Nov. 14, 2014; U.S. Provisional Application No. 62/089,080, "DIAGNOSTIC AND IMAGING DIRECTION BASED ON ANATOMICAL AND/OR PHYSIOLOGICAL PARAMETERS" filed Dec. 8, 2014; and U.S. Provisional Application No. 62/089,090, "AUTOMATED IDENTIFICATION AND CLASSIFICATION OF INTRAVASCULAR LESIONS" filed Dec. 8, 2014, the entireties of which are hereby incorporated by reference herein.

The system 100 includes an external imaging device 180. In various embodiments, the external imaging device 180 can include an x-ray system, angiography system, a rotational angiography system, fluoroscopy system, computed tomography (CT) system, a magnetic resonance imaging (MRI) system, other suitable imaging devices, and/or combinations thereof. The external imaging device 180 can be configured to acquire imaging data of anatomy, such as the heart and blood vessels. The imaging data can be visualized in the form of two-dimensional and/or three-dimensional images of the heart, blood vessel, and/or other anatomy.

The system 100 also includes a cardiac test imaging device 170. Generally, the cardiac test imaging device 170 can be associated with any non-invasive cardiac stress test that provides images of the heart that are indicative of the health of the cardiac muscle or myocardium. In various embodiments, the cardiac test imaging device can include a nuclear medicine imaging device, such as a gamma camera or a single-photon emission computed tomography (SPECT) system, other suitable devices, and/or combinations thereof. The cardiac test imaging device 170 can be configured to acquire myocardial perfusion imaging (MPI) data, multi-gated acquisition (MUGA) scan, radionuclide stress test, nuclear stress test, other cardiac stress data or diagnostic data, and/or combinations thereof. For example, MPI data can be collected by imaging a radiopharmaceutical agent, such as thallium, in the patient's heart muscle using a SPECT system. As illustrated, for example, in FIG. 8, the MPI data can be visualized in the form of a series of two-dimensional images. The images can illustrate muscle mass with normal blood flow during exercise and rest, normal blood flow during rest but not exercise, low blood flow during rest and exercise, and/or lack of blood flow (and radioactive dye) in areas of the heart due to scar tissue. As described herein, the cardiac test data or myocardial data can also be visualized in a three-dimensional manner.

In some embodiments, one or more of the cardiac test imaging device 170, the external imaging device 180, and/or the instruments 130 and 140 are located proximate one or more of the computing device 110, the display device 150, and/or the input device 160, such as in the same procedure room. In some embodiments, one or more of the cardiac test imaging device 170, the external imaging device 180, and/or the instruments 130 and 140 are located spaced from one or more of the computing device 110, the display device 150, and/or the input device 160, such as in different procedure rooms or facilities. For example, the cardiac test imaging device 170, the external imaging device 180, and/or the instruments 130 and 140 can be part of different systems that are communicatively coupled. In that regard, the computing device 160 can be configured to acquire the data collected from the components spaced therefrom and process the data as described herein. The cardiac test imaging device 170, the external imaging device 180, and/or the instruments 130 and 140 can be configured to transmit the collected data to the computing device 160.

The computing device 110 can include one or more software modules 112, 114, 116, 118, 120, 122, and 124. The software modules can include computer executable instructions associated with performing functions described herein, such as the functions associated the instruments 130 and 140, the cardiac test imaging device 170, and the external imaging device 180. For example, the computing device 110 can include a cardiac test module 112, an external imaging module 114, a physiology measurement module 116, an intravascular imaging module 118, and a lumen module 120. The cardiac test module 112 includes computer instructions for controlling the acquisition, receipt, and processing of the cardiac test data or myocardial data from the cardiac test imaging device 170, as well as instructions for generating a three-dimensional model and/or graphical representation of the cardiac test or myocardial data. The external imaging module 114 includes computer instructions for controlling the acquisition, receipt, and processing of the external imaging data from the external imaging device 180, as well as instructions for generating a three-dimensional model and/or graphical representation of the heart, blood vessels, and/or other anatomy.

The physiology measurement module 116 includes computer instructions for controlling the acquisition, receipt, and processing of the physiology measurements acquired by the instruments 130 and/or 140, as well as calculating one or more physiology quantities computed based on the acquired physiology measurements. The physiology quantities can include pressure-related values, flow-related values, etc. Pressure-related values can include FFR (e.g., a pressure ratio value calculated as a first instrument is moved through a vessel relative to a second instrument, including across at least one stenosis of the vessel), Pd/Pa (e.g., a ratio of the pressure distal to a lesion to the pressure proximal to the lesion), iFR (e.g., a pressure ratio value calculated using a diagnostic window relative to a distance as a first instrument is moved through a vessel relative to a second instrument, including across at least one stenosis of the vessel), etc. Flow-related values can include coronary flow reserve or CFR (e.g., maximum increase in blood flow through the coronary arteries above the normal resting volume), basal stenosis resistance index (BSR), etc. The physiology measurement module 116 also includes computer instructions to generate a graphical representation of the location and/or the numeral value associated with the physiology measurements and/or quantities.

The intravascular imaging module 118 includes computer instructions for controlling the acquisition, receipt, and processing of the intravascular imaging data acquired by the instruments 130 and 140. The computing device 110 can include various imaging modules to process data associated with different imaging modalities. The intravascular imaging module 118 can also include computer instructions for generating a three-dimensional model and/or graphical representation of the heart, blood vessels, and/or other anatomy based on the intravascular imaging data, including plaque structure, plaque composition, vessel size, native vessel size, etc. In that regard, the computing device 110 includes a tissue characterization module 122 that includes computer instructions to facilitate the determination of plaque structure and plaque composition. Methods and systems for recognizing tissues and tissue types in both diagnostic and therapeutic applications are described, for example, in U.S. patent application Ser. No. 14/209,915, "PARALLELIZED TREE-BASED PATTERN RECOGNITION FOR TISSUE CHARACTERIZATION," filed Mar. 13, 2014; U.S. Pat. No. 6,200,268 entitled "VASCULAR PLAQUE CHARACTERIZATION;" U.S. Pat. No. 6,381,350 entitled "INTRAVASCULAR ULTRASONIC ANALYSIS USING ACTIVE CONTOUR METHOD AND SYSTEM;" U.S. Pat. No. 7,074,188 entitled "SYSTEM AND METHOD OF CHARACTERIZING VASCULAR TISSUE;" U.S. Pat. No. 7,175,597 entitled "NON-INVASIVE TISSUE CHARACTERIZATION SYSTEM AND METHOD;" U.S. Pat. No. 7,215,802 entitled "SYSTEM AND METHOD FOR VASCULAR BORDER DETECTION;" U.S. Pat. No. 7,359,554 entitled "SYSTEM AND METHOD FOR IDENTIFYING A VASCULAR BORDER;" U.S. Pat. No. 7,627,156 entitled "AUTOMATED LESION ANALYSIS BASED UPON AUTOMATIC PLAQUE CHARACTERIZATION ACCORDING TO A CLASSIFICATION CRITERION;" and U.S. Pat. No. 7,988,633 entitled "APPARATUS AND METHOD FOR USE OF RFID CATHETER INTELLIGENCE," the entireties of which are hereby incorporated by reference herein.

The lumen module 120 includes computer instructions for controlling the acquisition, receipt, and processing of lumen data acquired by the instruments 130 and 140, and/or the external imaging device 180. The lumen data can include various information describing the blood flow region of a vessel, including the lumen dimensions, boundaries, contours, etc. The computing device 110 can utilize the tissue characterization module 122 in conjunction with the lumen module 120 to determine information about the blood flow region of the vessel. The lumen module 120 can also include computer instructions for generating a three-dimensional model and/or graphical representation of the vessel. In some embodiments, the intravascular imaging module 118 and the lumen module 120 are combined.

The co-registration module 124 includes computer instructions for correlating or co-registering the diagnostic information, such as physiology measurements, the computed physiology quantities, and/or the intravascular imaging data, to the external imaging data. In various embodiments, the external imaging data can include externally-obtained angiographic images, x-ray images, CT images, PET images, MRI images, SPECT images, and/or other two-dimensional or three-dimensional extra-luminal depictions of a patient's vasculature. Spatial co-registration can be completed using techniques disclosed in U.S. Pat. No. 7,930,014, titled "VASCULAR IMAGE CO-REGISTRATION," which is hereby incorporated by reference in its entirety, based on the known pullback speed/distance, based on a known starting point, based on a known ending point, and/or combinations thereof. For example, a mechanical pullback device can be used to conduct the pressure-sensing procedure. The mechanical pullback device can move the pressure-sensing device through the vessel at a fixed, known rate. The location of the pressure measurements and/or the pressure ratio(s) can be determined based on the rate of the pullback and a known location of the pressure-sensing device (e.g., a start position, a mid-point position, an end position, available from angiography data). In some embodiments, diagnostic information and/or data is correlated to vessel images using techniques similar to those described in U.S. Provisional Patent Application No. 61/747,480, titled "SPATIAL CORRELATION OF INTRAVASCULAR IMAGES AND PHYSIOLOGICAL FEATURES" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety.

In some embodiments, diagnostic information and/or data is correlated to vessel images using techniques similar to those described in U.S. patent application Ser. No. 14/144,280, titled "DEVICES, SYSTEMS, AND METHODS FOR ASSESSMENT OF VESSELS" and filed Dec. 31, 2012, which is hereby incorporated by reference in its entirety. In some embodiments, co-registration and/or correlation can be completed as described in U.S. Provisional Patent Application No. 61/856,509, titled "DEVICES, SYSTEMS, AND METHODS FOR ASSESSMENT OF VESSELS" and filed Jul. 19, 2013, which is hereby incorporated by reference in its entirety. In other embodiments, co-registration and/or correlation can be completed as described in International Application No. PCT/IL2011/000612, titled "CO-USE OF ENDOLUMINAL DATA AND EXTRALUMINAL IMAGING" and filed Jul. 28, 2011, which is hereby incorporated by reference in its entirety. Further, in some embodiments, co-registration and/or correlation can be completed as described in International Application No. PCT/IL2009/001089, titled "IMAGE PROCESSING AND TOOL ACTUATION FOR MEDICAL PROCEDURES" and filed Nov. 18, 2009, which is hereby incorporated by reference in its entirety. Additionally, in other embodiments, co-registration and/or correlation can be completed as described in U.S. patent application Ser. No. 12/075,244, titled "IMAGING FOR USE WITH MOVING ORGANS" and filed Mar. 10, 2008, which is hereby incorporated by reference in its entirety.

The system 100 includes a display device 150 that is communicatively coupled to the computing device 110. In some embodiments, the display device 150 is a component of the computing device 110, while in other embodiments, the display device 150 is distinct from the computing device 110. In some embodiments, the display device 150 is a holographic display device configured to output a three-dimensional graphical representation of the heart, blood vessels, and/or other anatomy. Any suitable holographic device within the scope of this disclosure, including self-contained monitors, projection/screen systems, head-up display systems, etc. The holographic device can implement principles based on moving reflective microelectromechanical systems (MEMS), laser plasma, electro-holography, etc. In some embodiments, the display device 150 is implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. The bedside controller can be configured to output a two-dimensional image and/or a two-dimensional representation of a three-dimensional model of the heart, blood vessels, and/or other anatomy. In some embodiments, the display device 150 is a monitor integrated in a console device or a standalone monitor (e.g., a flat panel or flat screen monitor). The computing device 110 can be configured to general visual displays based on the data collected by the instruments 130 and 140, the cardiac test imaging device 170, and/or the external imaging device 180. Exemplary visual displays (e.g., holographic displays, screen displays outputted by the bedside controller, etc.) are illustrated in FIGS. 4-9. The computing device 110 can generate and provide the display data associated with the visual displays to the display device 150.

The system 100 includes an input device 160 that is communicatively coupled to the computing device 110. The input device permits a user to interact with the visual displays outputted by the display device 150. For example, the user can provide a user input to select, modify, and/or manipulate all or a portion of the visual display using the input device. In some embodiments, user interface device is a separate component from the display device 180. For example, input device can be camera configured to acquire a clinician's hand gestures, such as the rotate, pan, and/or zoom in/out on a three-dimensional holographic display. Any suitable camera can be utilized, such as an RGB camera, infrared camera, etc. The input device can include processing equipment to interpret the hand gesture acquired by the input device. The computing device 110 can receive data representative of the hand gesture. The input device can also be any peripheral device, include a touch sensitive pad, keyboard, mouse, trackball, etc. In other embodiments, the user interface device is part of the display device 180. For example, the user interface device can be implemented as a bedside controller having a touch-screen display as described, for example, in U.S. Provisional Application No. 62/049,265, titled "Bedside Controller for Assessment of Vessels and Associated Devices, Systems, and Methods," and filed Sep. 11, 2014, the entirety of which is hereby incorporated by reference herein. In such embodiments, a user input can be a touch input received on the touch sensitive display of the bedside controller. The computing device 110 can receive data representative of the user touch input.

The system 100 can include various connectors, cables, interfaces, connections, etc., to communicate between the one or more sensors, transducers, and/or other monitoring elements of the instruments 130 and 140, the computing device 110, the cardiac test imaging device 170, the external imaging device 180, the display device 150, and/or the input device 160. The illustrated communication pathways are exemplary in nature and should not be considered limiting in any way. In that regard, it is understood that any communication pathway between the components of system 100 may be utilized, including physical connections (including electrical, optical, and/or fluid connections), wireless connections, and/or combinations thereof. In that regard, it is understood that the one or more of the components of the system 100 can communicate via a wireless connection in some instances. In some instances, the one or more components of the system 100 and/or the system 100 and other systems (e.g., of a hospital or health services provider) communicate via a communication link over a network (e.g., intranet, internet, telecommunications network, and/or other network). Various communication configurations are described, for example, in U.S. Provisional Application No. 62/080,023, "PERCUTANEOUS CORONARY INTERVENTION (PCI) PLANNING INTERFACE AND ASSOCIATED DEVICES, SYSTEMS, AND METHODS," filed Nov. 14, 2014, and U.S. Provisional Application No. 62/080,045, "PERCUTANEOUS CORONARY INTERVENTION PLANNING (PCI) PLANNING INTERFACE WITH PRESSURE DATA AND VESSEL DATA AND ASSOCI- ATED DEVICES, SYSTEMS, AND METHODS," filed Nov. 14, 2014, the entireties of which are hereby incorporated by reference herein.

Figure 2:
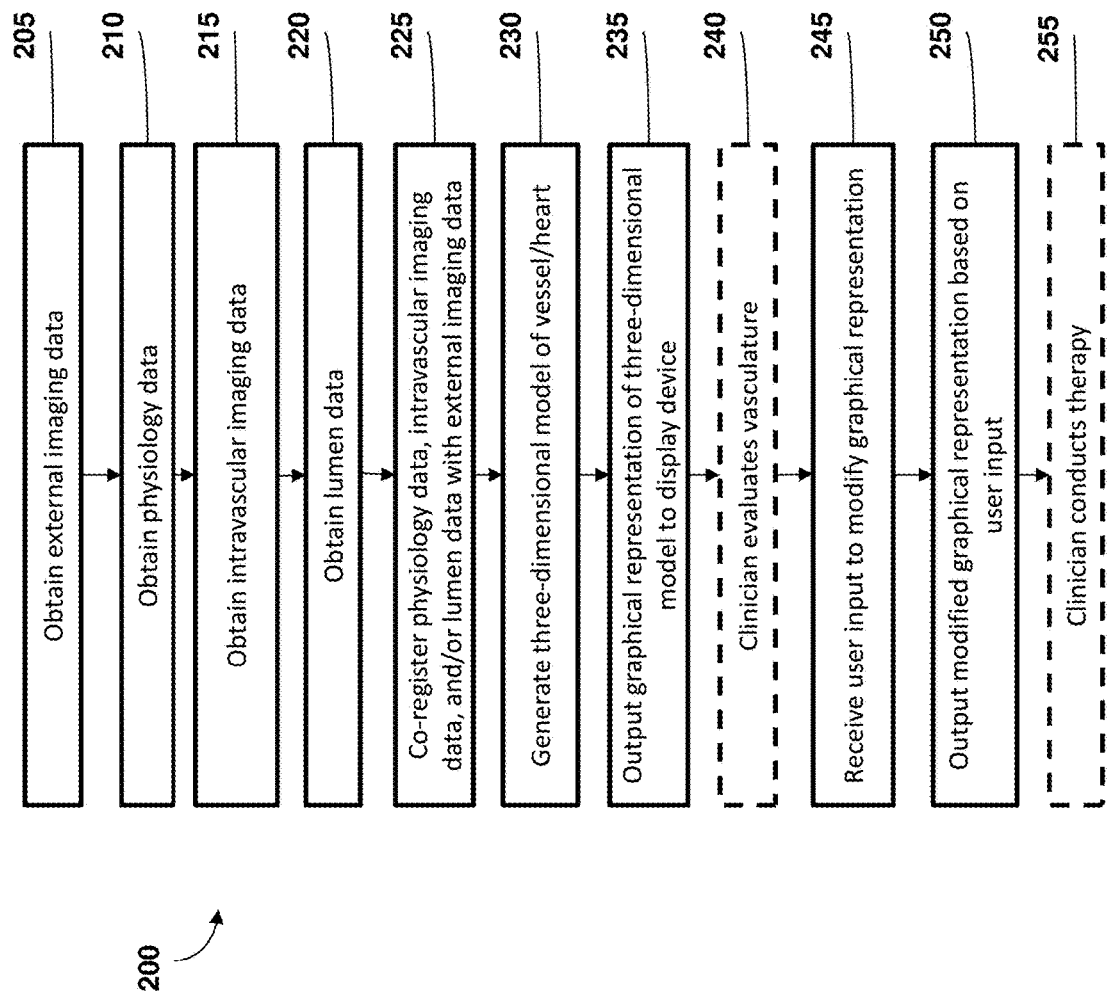
FIG. 2 is a flow diagram of a method of evaluating vasculature of a patient according to an embodiment of the present disclosure.

FIG. 2 is a flow diagram illustrating a method 200 of evaluating vasculature of a patient. As illustrated, the method 200 includes a number of enumerated steps, but embodiments of the method 200 may include additional steps before, after, and in between the enumerated steps. In some embodiments, one or more of the enumerated steps may be omitted or performed in a different order. One or more steps of the method 200 can be carried out by the computing device 110 (FIG. 1). At step 205, the method 200 includes obtaining external imaging data. For example, the computing device 110 can obtain angiographic and/or CT images of the heart, blood vessels, and/or other anatomy using the external imaging device 180 (FIG. 1). At step 210, the method 200 includes obtaining physiology data. For example, the computing device 110 can obtain pressure, flow, and/or other suitable physiologic data using one or both of the instruments 130 and 140.

For example, a clinician can insert pressure-sensing intravascular device(s), such as a catheter or guidewire, into the patient. In some embodiments, the clinician may guide the intravascular device within the patient to a desired position using the obtained external imaging data. After the pressure sensing intravascular device has been appropriately positioned in the patient, the clinician can initiate collection of pressure measurements. Pressure measurements can be collected during one or more of the following procedures: an FFR "spot" measurement where the pressure sensor stays in one place while hyperemia is induced; an FFR pullback in which an elongated period of hyperemia is induced and the sensor is pulled back to the ostium; an iFR "spot" measurement that is similar to the FFR spot measurement but without hyperemia; and an iFR pullback which is that the FFR pullback but without hyperemia. In various embodiments, physiological measurement collection can be carried through a combination of one or more of the procedures described above. Physiological measurement can be continuous, such as during a pullback procedure. Physiological measurements can occur while the intravascular device is moved in one direction. Measurement collection can be discontinuous procedure, such as when the intravascular device is selectively moved through the vessel (e.g., when movement of the intravascular device starts and stops, when the intravascular device is held at various points along the vessel longer than others, etc.). Physiological measurements can occur while the intravascular device is moved in both directions (e.g., proximally and distally within the blood vessel). Co-registration can be used to ensure that, regardless of how the physiological measurements were collected, the location of the measurement can be identified on an angiographic image of the vessel. For example, a composite of the collected physiological measurements can be generated based on the co-registered data.

In that regard, in some instances the pressure measurements are representative of a pressure ratio between a fixed location within the vessel and the moving position of the instrument as the instrument is moved through the vessel. For example, in some instances a proximal pressure measurement is obtained at a fixed location within the vessel while the instrument is pulled back through the vessel from a first position distal of the position where the proximal pressure measurement is obtained to a second position more proximal than the first position (i.e., closer to the fixed position of the proximal pressure measurement). For clarity in understanding the concepts of the present disclosure, this arrangement will be utilized to describe many of the embodiments of the present disclosure. However, it is understood that the concepts are equally applicable to other arrangements as described, for example, in are described, for example, in U.S. Provisional Application No. 62/080,023, "PERCUTANEOUS CORONARY INTERVENTION (PCI) PLANNING INTERFACE AND ASSOCIATED DEVICES, SYSTEMS, AND METHODS," filed Nov. 14, 2014, and U.S. Provisional Application No. 62/080,045, "PERCUTANEOUS CORONARY INTERVENTION PLANNING (PCI) PLANNING INTERFACE WITH PRESSURE DATA AND VESSEL DATA AND ASSOCIATED DEVICES, SYSTEMS, AND METHODS," filed Nov. 14, 2014, the entireties of which are hereby incorporated by reference herein.

In typical embodiments, a processing system can collect raw physiological data, such as pressure data, from the intravascular device and process the data to compute physiological quantitates, such as pressure differential(s) or ratio(s). For example, the pressure differential between the two pressure measurements within the vessel (e.g., a fixed location pressure measurement and a moving pressure measurement) is calculated as a ratio of the two pressure measurements (e.g., the moving pressure measurement divided by the fixed location pressure measurement), in some instances. In some instances, the pressure differential is calculated for each heartbeat cycle of the patient. In that regard, the calculated pressure differential is the average pressure differential across a heartbeat cycle in some embodiments. For example, in some instances where a hyperemic agent is applied to the patient, the average pressure differential across the heartbeat cycle is utilized to calculate the pressure differential. In other embodiments, only a portion of the heartbeat cycle is utilized to calculate the pressure differential. The pressure differential is an average over the portion or diagnostic window of the heartbeat cycle, in some instances.

In some embodiments a diagnostic window is selected using one or more of the techniques described in U.S. patent application Ser. No. 13/460,296, filed Apr. 30, 2012 and titled "DEVICES, SYSTEMS, AND METHODS FOR ASSESSING A VESSEL," which is hereby incorporated by reference in its entirety. As discussed therein, the diagnostic windows and associated techniques are particularly suitable for use without application of a hyperemic agent to the patient. In general, the diagnostic window for evaluating differential pressure across a stenosis without the use of a hyperemic agent is identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

Referring again to FIG. 2, at step 215, the method 200 includes obtaining intravascular imaging data. The intravascular imaging data, such as IVUS or OCT data, can be collected using one or both of the instruments 130 and 140, in a similar manner as the physiology data is collected (step 210). For example, the some embodiments, a clinician can insert intravascular device(s), such as a catheter or guidewire, with imaging components into the patient. In some embodiments, the clinician may guide the intravascular device within the patient to a desired position using the external imaging data. After the intravascular device has been appropriately positioned in the patient, the clinician can initiate collection of imaging data. The intravascular images can be acquired in a continuous manner, such as during a pullback procedure. The intravascular imaging data can be cross-sectional images, forward-looking images, side-looking images, etc.

In some embodiments, the physiology data and/or the intravascular imaging data are obtained simultaneously. For example, one or both of the instruments 130 and 140 can include a pressure transducer as well as an imaging component. When at least one of the instruments 130 and 140 is moved longitudinally through the vessel, the instrument can simultaneously acquire both pressure measurements and intravascular images. In some embodiments, the physiology data and/or the intravascular imaging data are obtained simultaneously as the external imaging data is acquired. Simultaneously collecting external imaging data and physiology data and/or the intravascular imaging data can facilitate co-registration, as described above. For example, the collected pressure data can be co-registered such that the location of the pressure sensing or imaging component of the intravascular device within the vessel is known. The computing device 110 can associate the location with the intravascular images, the pressure measurements and/or the pressure ratio(s) at that location. The computing device 110 can also generate a visual display including respective indicators representative of the location of the intravascular images, the pressure measurements, and/or the pressure ratio(s), as described herein.

At step 220, the method 200 includes obtaining lumen data. For example, the computing device 110 can utilize the obtained external imaging data and/or the intravascular imaging data to determine information about the blood flow region of the blood vessel, such as lumen dimensions, boundaries, contours. At step 225, the method 200 includes co-registering the physiology data, the intravascular imaging data, and/or the lumen data with the external imaging data. For example the computing device 110 can co-register the obtained physiology data, intravascular imaging data, and/or the lumen data with a physical location in the vessel using the obtained external imaging data.

At step 230, the method 200 includes generating a three-dimensional model of the heart, blood vessel, and/or other anatomy. The model can be a data representation or visual representation of one or more components of the vessel 100. The computing device 110 is configured to generate the three-dimensional model using the obtained external imaging data, the co-registered physiology data, and/or the co-registered intravascular imaging data. For example, the external imaging data (e.g., CT, rotational angiography) can be used to generate three-dimensional information regarding the anatomy, such as external vessel dimensions, internal lumen dimensions, position, contours, etc. The position and/or viewing angle of the external imaging system can also be used to generate three-dimensional information. The intravascular imaging data and/or lumen data can be used to generate additional three-dimensional information regarding the anatomy, such as anatomical structure, vessel borders, tissue characterization, internal lumen dimensions, lumen size, lumen dimensions, lesion location, lesion severity, lesion length, etc. Because the intravascular imaging data and/or lumen data is co-registered, the intravascular imaging data, the lumen data, and/or the external imaging data can be combined to generate to a complete three dimensional model. For example, the external dimensions of a vessel determined from the external imaging data can be combined with the internal structure of the vessel determined the intravascular imaging data. Generating the three-dimensional model can include position information of a blood-tissue boundary, a media-adventitia boundary, lumen border or wall, blood, plaque, adventitia, calcium, etc., as described, for example, in U.S. Provisional Application No. 62/024,339, "DEVICES, SYSTEM, AND METHODS FOR IMPROVED ACCURACY MODEL OF VESSEL ANATOMY," filed Jul. 14, 2014, the entirety of which is hereby incorporated by reference herein. In some embodiments, the computing device 110 can automatically recommend acquisition of additional intravascular imaging and/or physiologic data to generate a more accurate assessment of the anatomy as described, for example, in U.S. Provisional Application No. 62/089,080, "DIAGNOSTIC AND IMAGING DIRECTION BASED ON ANATOMICAL AND/OR PHYSIOLOGICAL PARAMETERS" filed Dec. 8, 2014, the entirety of which is hereby incorporated by reference herein.

At step 235, the method 200 includes outputting a three-dimensional graphical representation of the model to a display device. For example, the computing device 110 can generate display data associated with the graphical representation and provide the display data to the display device 150. The graphical representation can be displayed in a three-dimensional manner, such as in a holographic display, or as a two-dimensional version, such as on a monitor or touch-screen display. Exemplary visual displays including the three-dimensional graphical representation are illustrated in FIGS. 4-9. The three dimensional graphical representation can include the heart and coronary arteries (FIGS. 4, 7, and 9), a particular vessel or set of vessels (FIGS. 5-6), and/or other anatomy. In some embodiments, the graphical representation can include a cross-sectional view (FIG. 6) of the heart, vessel, and/or other anatomy.

At step 240, the method 200 includes the clinician evaluating the patient's vasculature. The three-dimensional model of the heart, vessel(s), and/or other anatomy provides an intuitive mechanism for virtually visualizing and comprehending the inside of a vessel in order to determine appropriate treatment without actually cutting open the vessel and/or the patient. For example, the clinician can interact with the three-dimensional graphical representation, e.g., via the input device 160, to determine the location, length, severity, and/or other characteristics of a lesion in a blood vessel. The clinician can also interact with the three-dimensional graphical representation to determine one or more parameters (e.g., length, diameter, position) associated with a stent to be positioned with the vessel. By providing an indicator identifying the location associated with the obtained physiology data and/or intravascular imaging data in the three-dimensional graphical representation, the clinician can utilize the physiology data and/or intravascular imaging data in a meaningfully integrated manner to determine the one or more parameters for a PCI.

In some embodiments, the computing device 110 can automatically identify a lesion in the vessel as described, for example, in U.S. Provisional Application No. 62/089,090, "AUTOMATED IDENTIFICATION AND CLASSIFICATION OF INTRAVASCULAR LESIONS" filed Dec. 8, 2014, the entirety of which is hereby incorporated by reference herein. The location, classification, and/or other determined information about the lesion can be outputted along with the three-dimensional graphical representation of the heart and/or vessel. In some embodiments, the computing device 110 can automatically determine PCI is the appropriate treatment for the vessel. Angiography data, pressure measurements, and/or other data can be used to determine that a vessel stenosis exists and that is it necessary to treat the vessel. Exemplary embodiments of determining to treat the vessel are described in U.S. Provisional Application No. 62/089,039, "DEVICES, SYSTEMS, AND METHODS FOR VESSEL ASSESSMENT AND INTERVENTION RECOMMENDATION" filed Dec. 8, 2014, the entirety of which is hereby incorporated by reference herein.

At step 245, the method 200 includes receiving a user input to modify the three-dimensional graphical representation. For example, the computing device 110 can receive data representative of a user touch input on a touch-sensitive display device. For example, the computing device 100 can receive data representative of a hand gesture obtained by an input device. For example, the computing device 100 can receive data representative of an input from a peripheral device. In that regard, the user input can be associated with a peripheral device such as a mouse, trackball, etc. to control two dimensional images displayed on a monitor (e.g., a flat display), a peripheral device such as a mouse, trackball, etc. to control three dimensional images displayed on a monitor (e.g., a flat display), a touch input on a touch sensitive display to control two dimensional images displayed on a monitor (e.g., a flat display), a touch input on a touch sensitive display to control three dimensional images displayed on a monitor (e.g., a flat display), a peripheral device such as a mouse, trackball, etc. to control three dimensional images displayed on a holographic (three-dimensional) display, and/or hand gestures within the holographic display area to control three dimensional images displayed on a holographic (three-dimensional) display.

A clinician can interact with and/or manipulate the three-dimensional graphical representation in a variety of ways. The clinician can provide a user input to rotate, pan, and/or zoom in/out on the graphical representation. For example, the computing device 110 can receive data representative of a hand gesture or touch input to rotate, pan, and/or zoom in/out on a three-dimensional graphical representation of a heart or blood vessel. The clinician can select a particular portion of the anatomy to view. For example, when the graphical representation includes a three-dimensional model of the heart, the computing device 110 can receive a user input to select a particular coronary artery. The clinician can select a particular view of the anatomy. For example, the computing device 110 can receive a user input to view a horizontal or vertical cross-sectional profile of a vessel. The clinician can measure one or more dimensions of the anatomy. For example, the computing device 110 can receive a user input to measure a length or diameter of a vessel. In some embodiments, the three dimensional graphical representation can include indicators representative of the location within the vessel where the physiology data and/or intravascular imaging data were acquired. The clinician can select one or more of the indicators to view the associated physiology data and/or intravascular imaging data.

At step 250, the method 200 includes outputting the modified graphical representation based on the user input. The computing device 110 can generate display data representative of the modified graphical representation. For example, the three-dimensional graphical representation of the heart, vessel, and/or other anatomy can be outputted in the orientation, position, and/or magnification based the user input to rotate, pan, and/or zoom in/out. For example, a coronary artery can be outputted when the particular artery is selected on the graphical representation of the heart. For example, a horizontal or vertical cross-sectional profile of a vessel can be outputted. For example, the value of a measurement and/or a graphical indicator representative of the measurement can be outputted in response to a user measurement input. For example, the obtained physiology data and/or intravascular imaging data can be outputted in response to a user input to select indicator(s) associated therewith in the graphical representation.

At step 255, the method 200 includes the clinician conducting the therapy based on the assessment of the patient's vasculature. For example, the clinician can conduct a PCI using one or more parameters (e.g., length, diameter, position) of a stent determined using the three-dimensional model of the vessel anatomy. For example, the length and/or diameter measurements of the vessel carried out on the graphical representation can be used to select the one or more parameters. In some embodiments, the computing device 110 is configured to provide simulated PCI planning to facilitate determination of the one or more parameters as described, for example, in U.S. Provisional Application No. 62/080,023, "PERCUTANEOUS CORONARY INTERVENTION (PCI) PLANNING INTERFACE AND ASSOCIATED DEVICES, SYSTEMS, AND METHODS," filed Nov. 14, 2014, and U.S. Provisional Application No. 62/080, 045, "PERCUTANEOUS CORONARY INTERVENTION PLANNING (PCI) PLANNING INTERFACE WITH PRESSURE DATA AND VESSEL DATA AND ASSOCIATED DEVICES, SYSTEMS, AND METHODS," filed Nov. 14, 2014, the entireties of which are hereby incorporated by reference herein.

Figure 3:
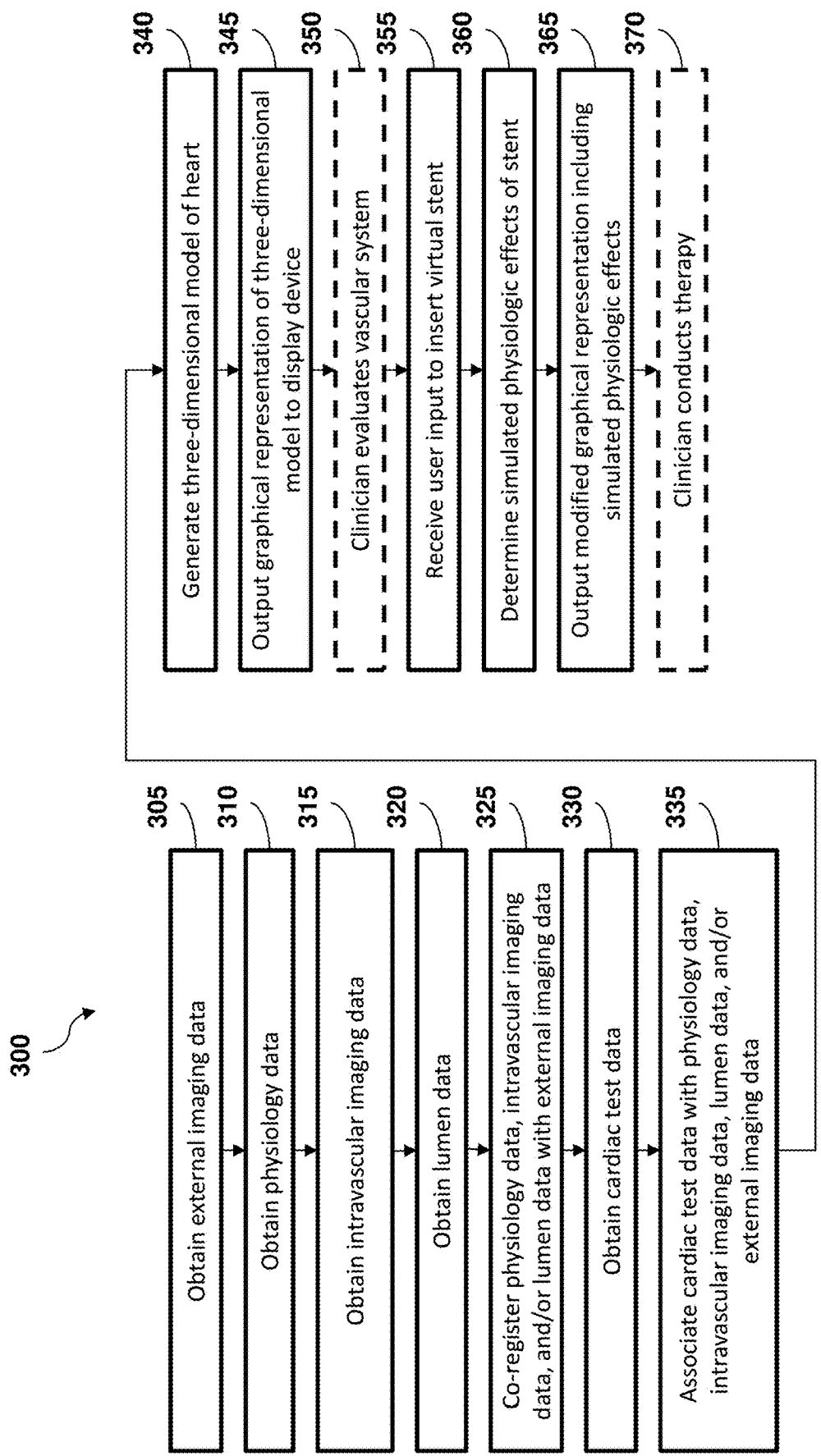
FIG. 3 is a flow diagram of a method of evaluating a vascular system of a patient according to an embodiment of the present disclosure.

FIG. 3 is flowchart illustrating a method 300 of evaluating a vascular system of a patient. As illustrated, the method 300 includes a number of enumerated steps, but embodiments of the method 300 may include additional steps before, after, and in between the enumerated steps. In some embodiments, one or more of the enumerated steps may be omitted or performed in a different order. The method 300 is similar to the method 200. One or more steps of the method 300 can be carried out by the computing device 110 (FIG. 1). Steps 305, 310, 315, 320, and 325 of the method 300 are similar to the steps 205, 210, 215, 220, and 225 of the method 200.

At step 330, the method 300 includes obtaining cardiac test data. For example, the computing device 110 can receive myocardial perfusion imaging (MPI) data. In some embodiments, the cardiac test data is obtained before the physiology data, intravascular imaging data, and/or lumen data (steps 310, 315, and 320) is collected. For example, the data associated with non-invasive procedures, such as the external imaging data and cardiac test data (steps 305 and 330), can be collected before the data associated with invasive procedures, such as the physiology data, intravascular imaging data, and/or the lumen data. In some embodiments, the cardiac test data can be obtained at the same time (e.g., during the same diagnostic appointment) as the external imaging data, physiology data, and/or intravascular imaging data is obtained. In some embodiments, any one or more of the external imaging data, physiology data, intravascular imaging data, and/or cardiac test data is obtained at a different time than the others. In that regard, the computing device 110 is configured to obtain data records from an earlier procedure such that the three-dimensional model of the heart, vessels, and/or other anatomy can be generated from different sources of information collected at different times. The computing device 110 can be communicatively coupled to a hospital or medical services provide network including a data store with the patient's medical records, diagnostic data, etc.

At step 335, the method 300 includes associating the cardiac test data with physiology data, intravascular imaging data, lumen data, and/or external imaging data. For example, with MPI data, the computing device 110 can associate portions of the myocardium with corresponding portions of the coronary arteries that supply blood. The portions of the coronary arteries can be identified using the physiology data, intravascular imaging data, lumen data, and/or external imaging data. The corresponding portions of the heart muscle can be identified using the MPI data. In some embodiments, the clinician can manually associate the coronary arteries with corresponding portions of the myocardium. In some embodiments, the computing device 110 can automatically determine the association. In the embodiment including MPI data, perfusion defects can be associated by their three dimensional location with the coronary vessels that are likely to supply blood to the under-perfused heart muscle area. This association is enhanced by the identification of the coronary vessels through noninvasive imaging and the creation of a three dimensional structure. As described below, the computing device 110 can use the association between the coronary arteries and the myocardium can be used to predict the physiologic effects of a simulated PCI on blood flow to the heart muscle.

Figure 8:
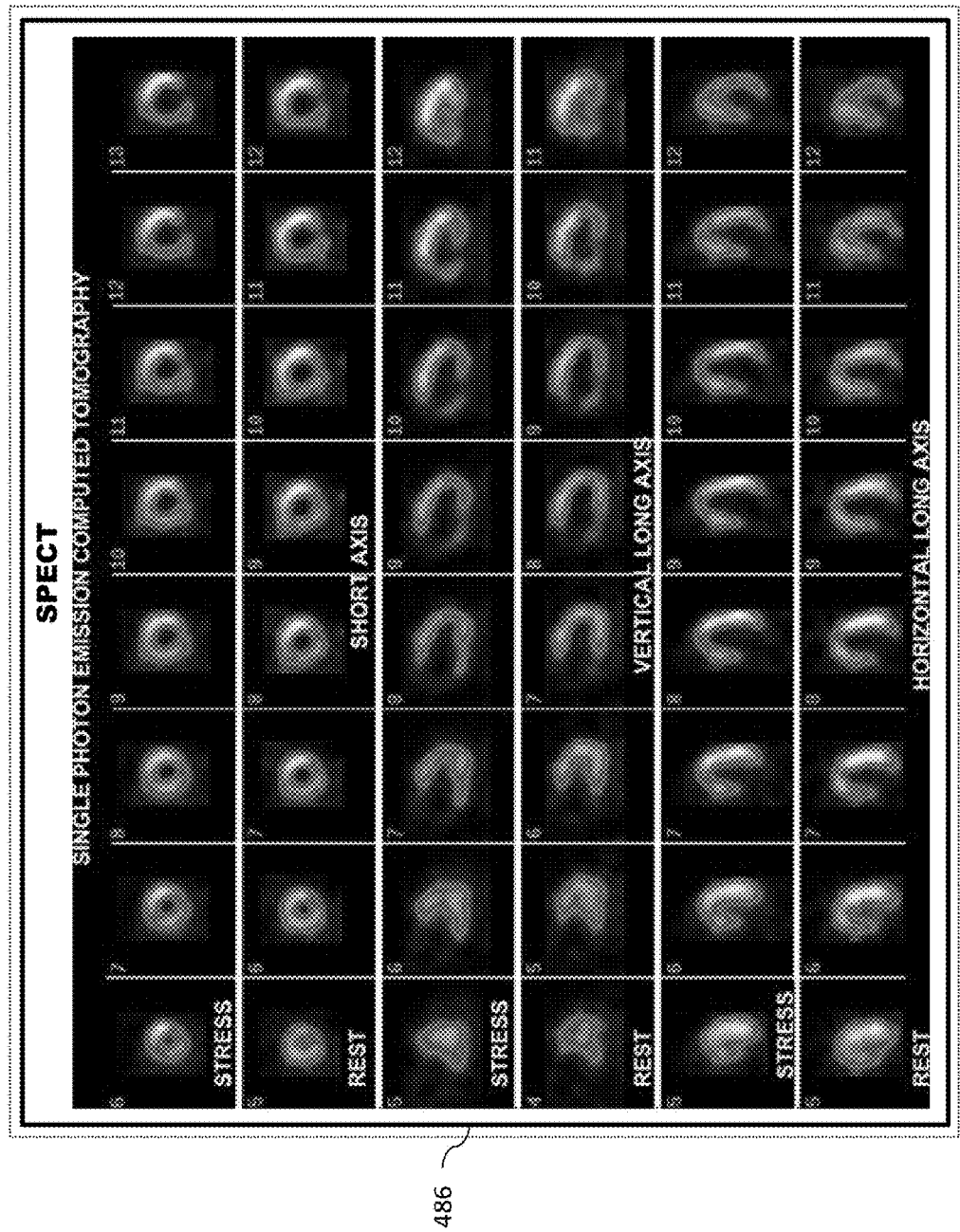
FIG. 8 is a visual display according to another embodiment of the present disclosure.

At step 340, the method 300 includes generating the three-dimensional model of heart. Step 340 is similar to step 230 of the method 200. Step 340 additionally includes generating a three-dimensional model of the cardiac test data. For example, MPI data can include planar slices along various axes (e.g., short axis, vertical long axis, horizontal long axis, etc.) of the heart, with different sets of images for different vascular states (e.g., stress, rest, etc.). Exemplary MPI data is illustrated in FIG. 8. The computing device 110 can combine the images to generate a three-dimensional model of the cardiac test data. In some embodiments, the computing device 110 can combine the cardiac test data with the physiology data, intravascular imaging data, lumen data, and/or external imaging data to generate the three-dimensional model of the heart. For example, the structure of the heart indicated by the cardiac test data can be used to verify and/or modify the structure of the heart generated based external imaging data.

Figure 7:
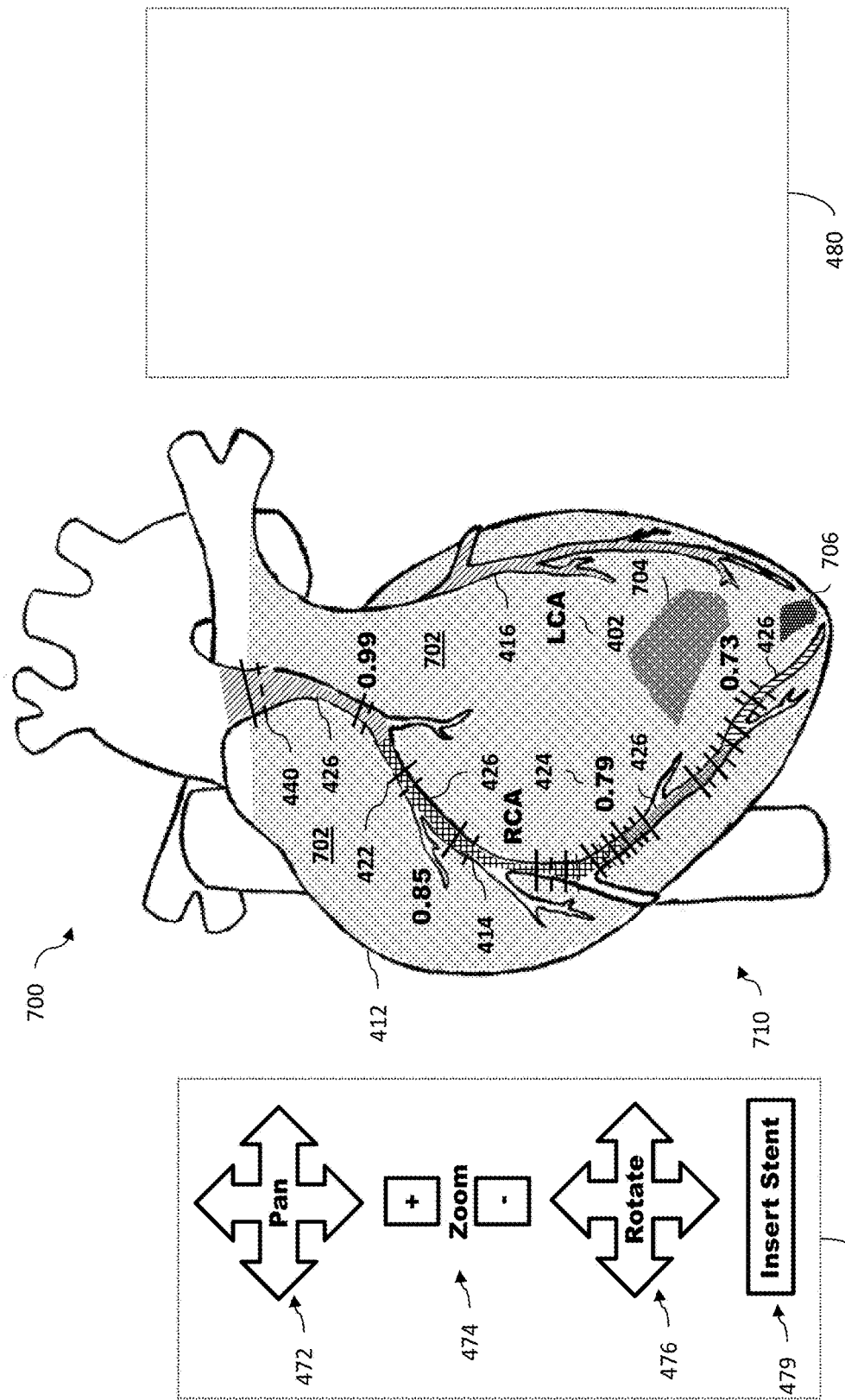
FIG. 7 is a visual display according to another embodiment of the present disclosure.
Figure 9:
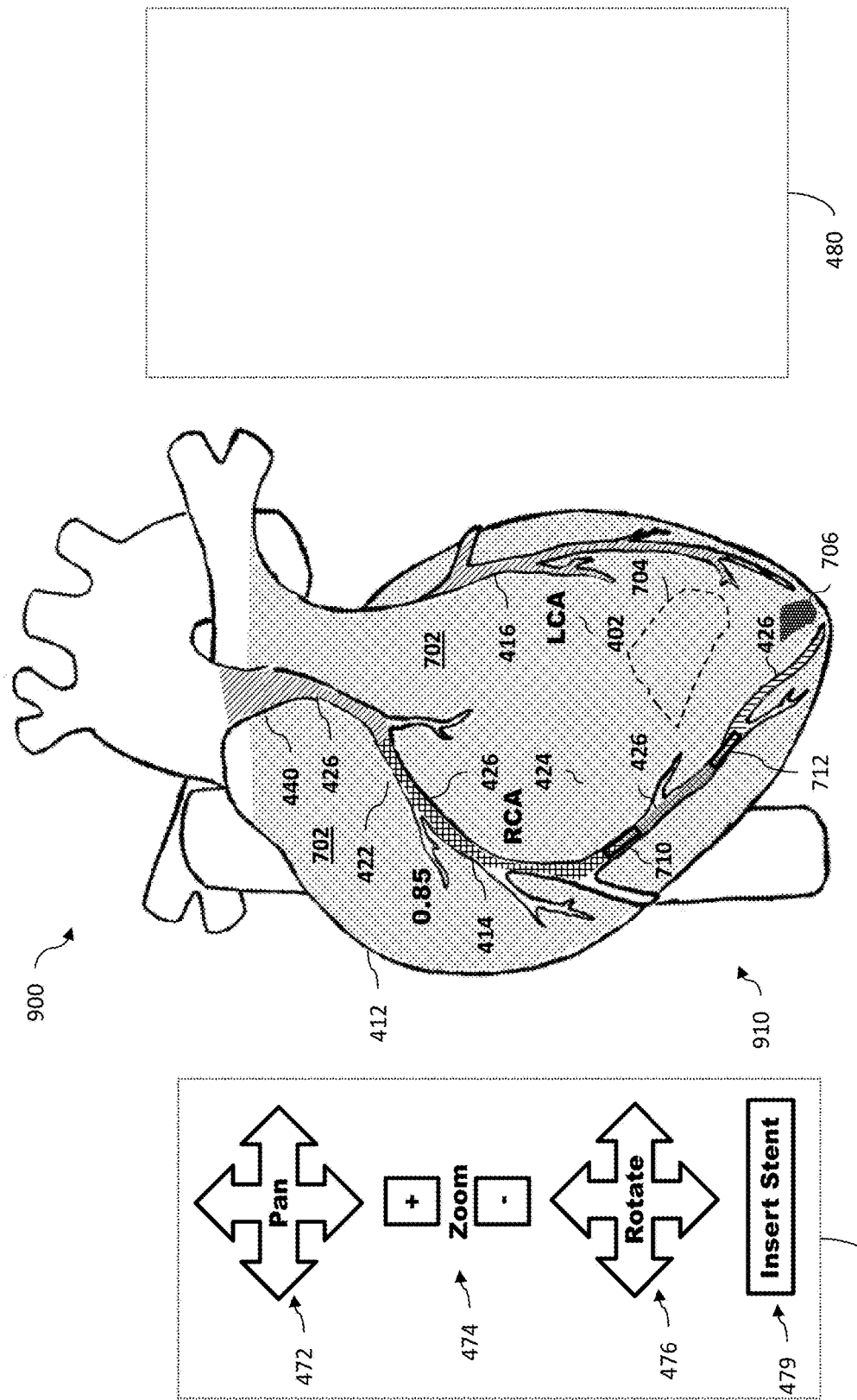
FIG. 9 is a visual display according to another embodiment of the present disclosure.

At step 345, the method 300 includes outputting a graphical representation of the three-dimensional model to the display device. Step 345 is similar to step 235 of the method 200. Step 345 additionally includes outputting a graphical representation of the three-dimensional model of the cardiac test data. The graphical representation can be displayed in a three-dimensional manner, such as in a holographic display, or as a two-dimensional version, such as on an external monitor or touch-screen display. Exemplary visual displays including a graphical representation of the cardiac test data are shown in FIGS. 7 and 9. As illustrated, the graphical representation of the cardiac test data can be provided in addition to the graphical representation of the heart and vessels.

At step 350, the method 300 includes the clinician evaluating the vascular system. Step 350 is similar to step 240 of the method 200. The clinician can additionally evaluate oxygenation of the heart muscle because the graphical representation includes the cardiac test data. Using the graphical representation of the cardiac test data and the heart, the clinician can identify portions of the heart muscle receiving an unhealthy amount of blood flow, which can be indicative of a lesion in a coronary artery. Because the cardiac test data is integrated with the physiologic data, intravascular imaging data, and external imaging data, the clinician can make a more complete assessment of the heart. The clinician can also predict the impact of revascularization, resulting from stent deployment, on the oxygenation of the heart muscle, as described with respect to steps 355, 360, and 365.

At step 355, the method 300 includes receiving a user input to insert a virtual/simulated stent in the graphical representation of the anatomy. The user input can be received in the form of one or more hand gestures, such as when the graphical representation of the heart is a holographic display, or in the form of a user touch input, such as when the graphical representation is outputted via a touch screen display device. In some embodiments, the computing device 110 automatically determines the parameters associated with the virtual stent, such as position, length, diameter, etc. In other embodiments, one or more parameters can be specified and/or changed by the clinician. PCI planning with simulated stent(s) is described in, for example, in U.S. Publication No. 2016/0135787, "PERCUTANEOUS CORONARY INTERVENTION (PCI) PLANNING INTERFACE AND ASSOCIATED DEVICES, SYSTEMS, AND METHODS," and U.S. Publication No. 2016/0135757 "PERCUTANEOUS CORONARY INTERVENTION PLANNING (PCI) PLANNING INTERFACE WITH PRESSURE DATA AND VESSEL DATA AND ASSOCIATED DEVICES, SYSTEMS, AND METHODS," the entireties of which are hereby incorporated by reference herein.

At step 360, the method 300 includes determining simulated physiologic effects associated with the simulated stent. For example, the computing device 110 can utilize the established association (step 335) between the coronary arteries and the myocardium to determine the simulated physiologic effects. The simulated stent can simulate the restoration of normal, healthy blood flow in a portion of a coronary artery. The coronary artery supplies blood to a portion of the heart muscle. Prior to occlusion being corrected by the stent, the portion of the heart muscle may not have received a healthy amount of blood/oxygen, as indicated in the cardiac test data and the graphical representation thereof. With the simulated stent restoring normal, healthy blood flow, the computing device 110 can determine the corresponding effect on blood/oxygen received by the portion of the heart muscle. In some circumstances, the heart muscle can return to normal, healthy amount of blood flow/oxygenation. In some circumstances, such as when the patient has previous experienced occlusions in the same coronary arteries, the heart muscle may be damaged and not return to normal, healthy amount of blood flow/oxygenation, even with the simulated stent. The computing device 110 can be configured to determine the simulated physiologic effects based on the determined parameters of the stent (e.g., length, diameter, position, etc.). Thus, the clinician can optimize the deployment of the stent by adjusting one or more of the parameters such that normal, healthy blood flow/oxygenation is returned to as much as the heart muscle as possible.

At step 365, the method 300 includes output modified graphical representation including simulated physiologic effects. The computing device 110 can generate display data representative of the modified graphical representation. For example, portions of the three-dimensional graphical representation of the cardiac test data can be modified to represent the return of normal, healthy blood flow as result of the simulated stent being deployed, as described with respect to FIG. 9.

The method 300 can also include receiving user input to interact with and/or manipulate the three-dimensional graphical representation in a variety of ways as described with respect to the method 200. For example, the computing device 110 can receive data representative of a hand gesture or touch input to rotate, pan, and/or zoom in/out on a three-dimensional graphical representation of a heart, including the graphical representation of the cardiac test data. For example, the computing device 110 can receive a user input to select a particular coronary artery, to view a cross-sectional profile of a vessel, etc. The computing device 110 can generate display data associated with the modified graphical representation and output it to the display device 150. At step 370, the method 300 includes the clinician conducting the therapy based on the assessment of the patient's vascular system. Step 370 is similar to step 255 of the method 200.

FIGS. 4-9 illustrate visual displays according to exemplary embodiments. All or a portion of the visual displays of FIGS. 4-9 can be three-dimensional, two-dimensional, and/or two-dimensional representations of three-dimensional models. In that regard, the visual displays can output by the display device 150, such as a holographic display device, an external display, a touch screen display device, etc. The computing device 110 can generate display data associated with the visual displays such that the display device 150 is configured to output the visual displays based on the display data.

Figure 4:
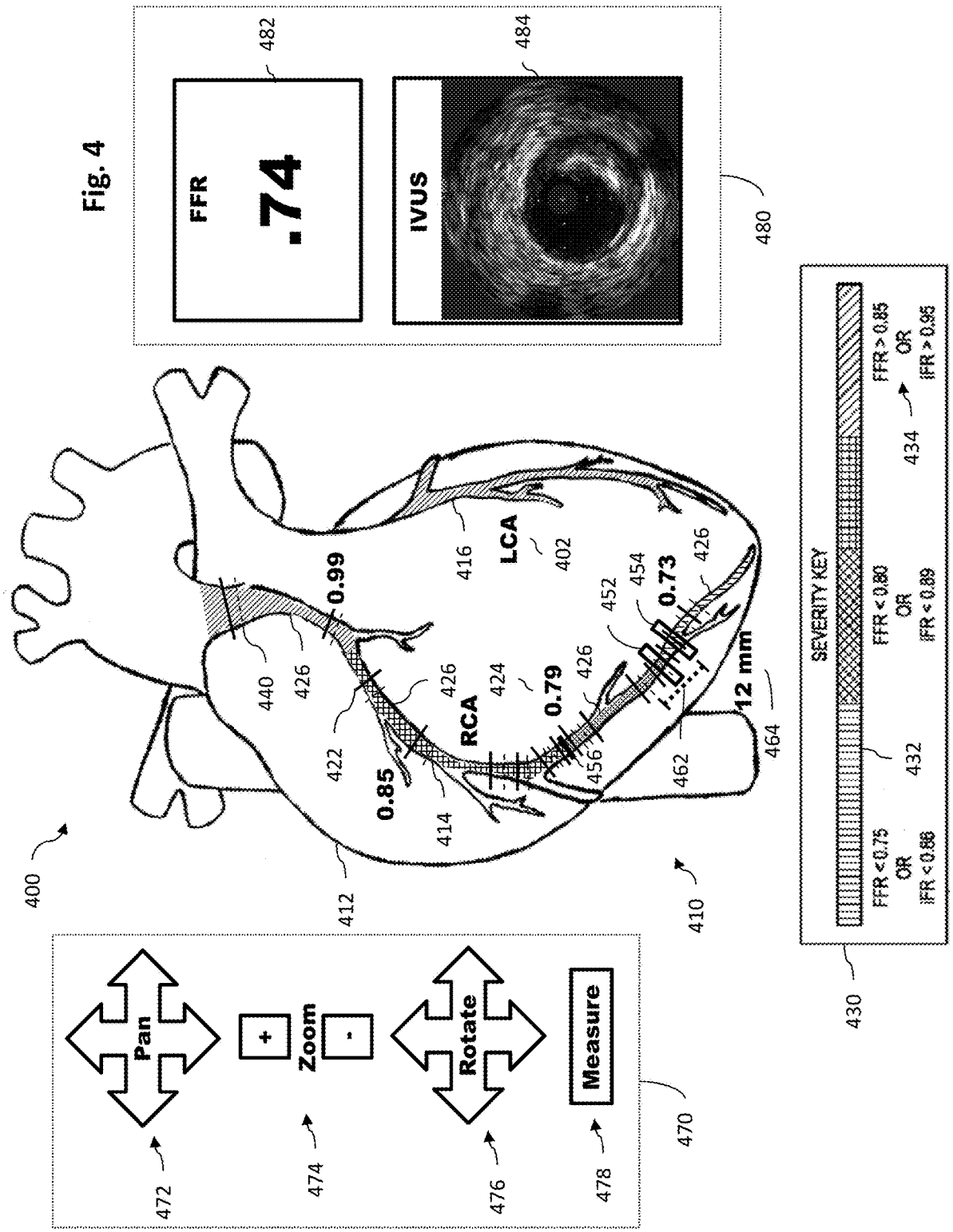
FIG. 4 is a visual display according to an embodiment of the present disclosure.

Referring now to FIG. 4, shown therein a visual display 400 including a graphical representation 410. The graphical representation 410 includes the heart 412 and one or more coronary arteries 414 and 416. The graphical representation of the heart 412 and/or the coronary arteries 414 can be three-dimensional representations generated based on the external imaging data, the intravascular imaging data, and/or the cardiac test data. The graphical representation of the heart 412 can be an anatomically correct and/or a stylized version of the anatomy.

In some embodiments, the computing device 110 can use the external imaging data, such as the contours, location, branches, and other features of the vessel(s) to automatically identify the vessel. The position and/or viewing angle of the external imaging system (e.g., angiography or x-ray system) can also be used to identify the vessel. The computing device 110 can generate the display data associated with the label 402, including alphabetical, numerical, alphanumeric, and/or symbolic characters. In the embodiment of FIG. 4, the labels 402 include an abbreviation of the identified vessel, such as "RCA" for right coronary artery and "LCA" for left coronary artery. While abbreviations and particular vessels are used in FIG. 4, it is understood that any suitable label can be used. In some embodiments, a user can selectively activate or deactivate one or more of the labels 402 such that a portion, all, or none of the labels 402 are included in the visual display 400.

Figure 5:
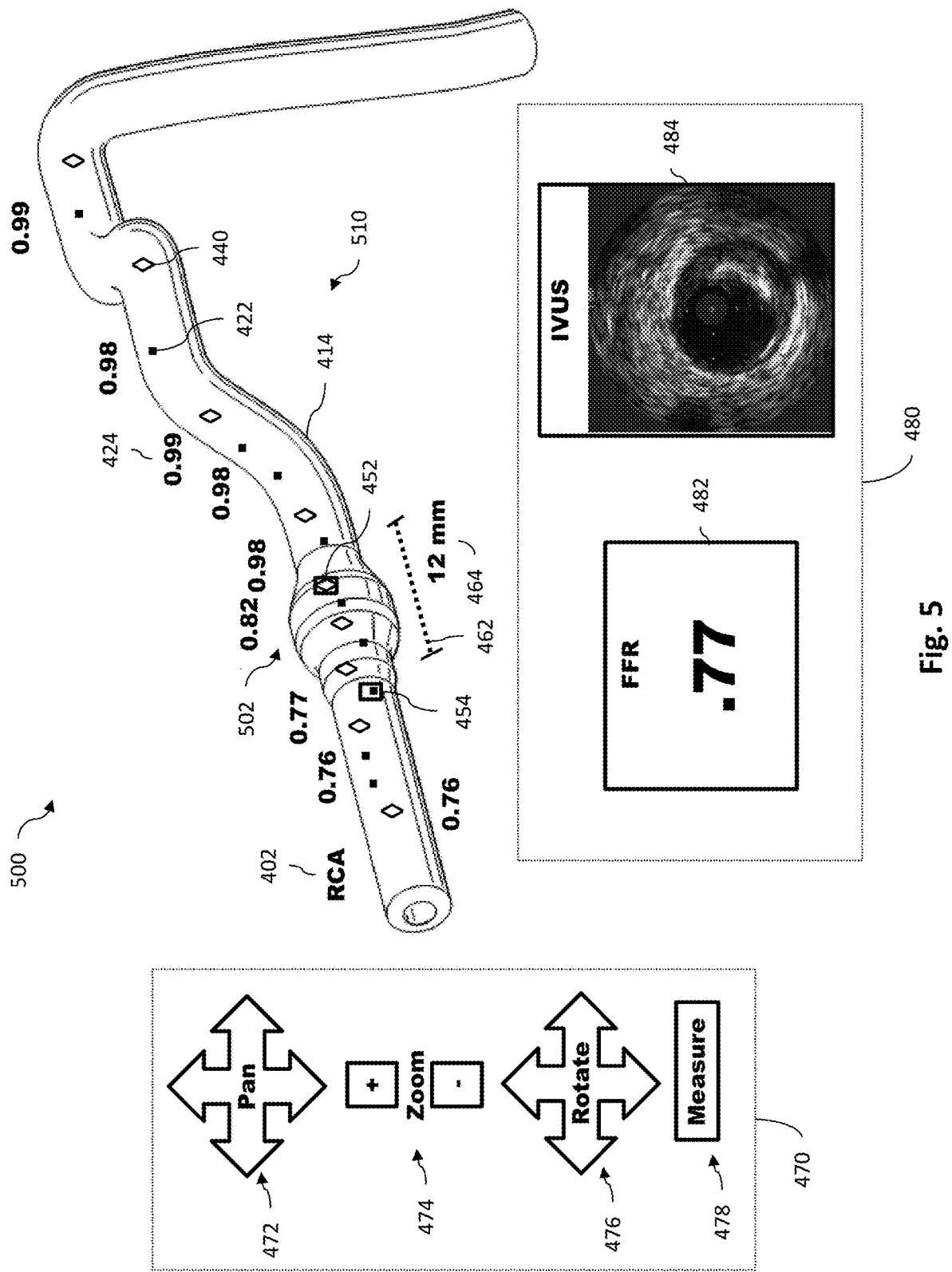
FIG. 5 is a visual display according to another embodiment of the present disclosure.
Figure 6:
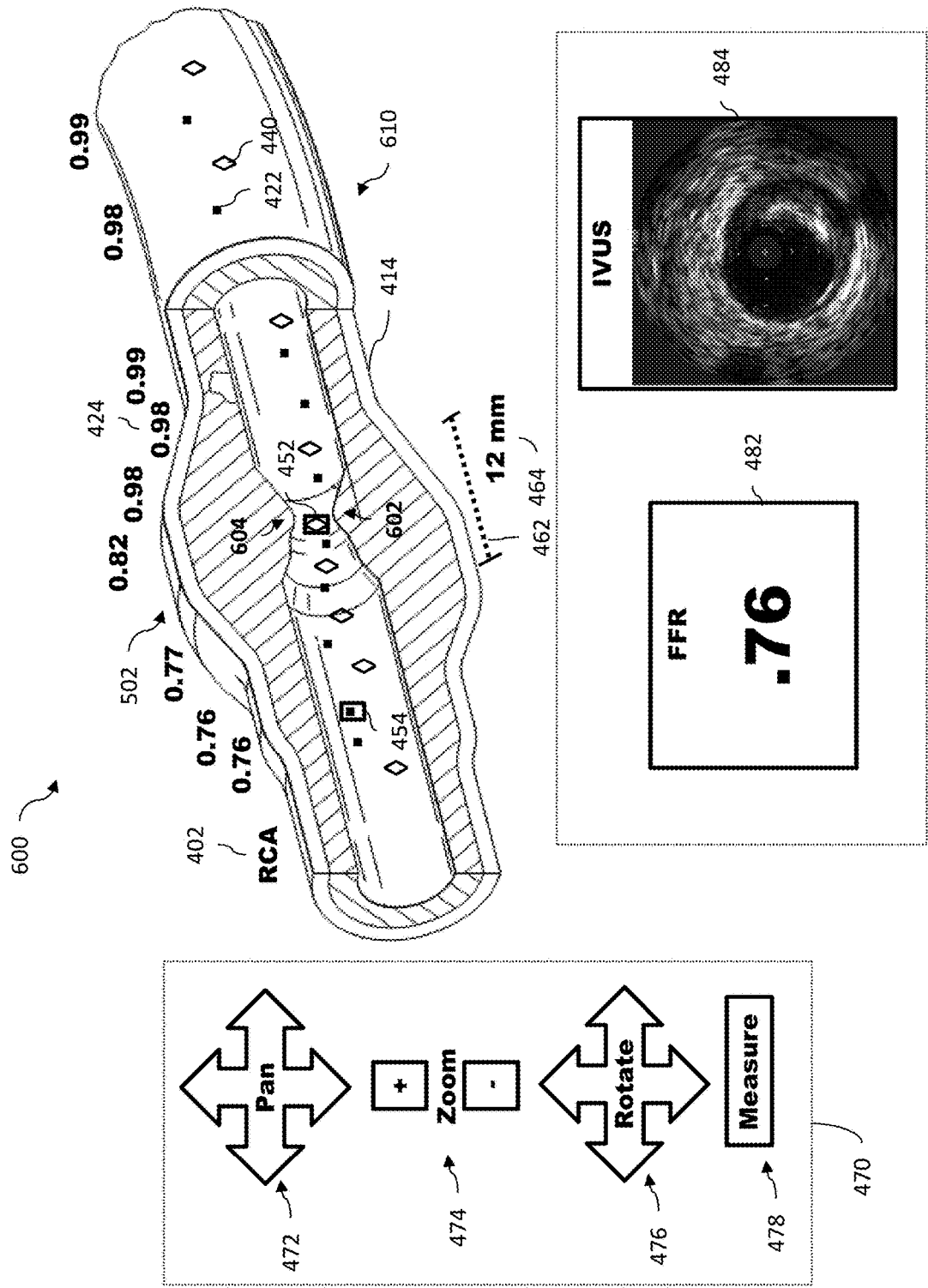
FIG. 6 is a visual display according to another embodiment of the present disclosure.

The visual display 400 also includes markers 422 indicative of a location within the vessel 414 associated with the collected physiology measurements or computed physiology quantities. For example, the markers 422 can be a location of the pressure sensor when the pressure measurements are collected. In the embodiment of FIGS. 4 and 7, the markers 422 are line segments that transect the vessel 414. In the embodiment of FIGS. 5 and 6, the markers 422 are symbols positioned along or within the vessel 414. While a square is shown in FIGS. 5 and 6, it is understood that any suitable shape or symbol can be used. Other examples of markers indicative of location are described in U.S. Provisional Application No. 61/895,909, titled "Devices, Systems, and Methods for Vessel Assessment," and filed Oct. 25, 2013, the entirety of which is hereby incorporated by reference herein. In some embodiments, a user can selectively activate or deactivate one or more of the markers 422 such that a portion, all, or none of the markers 422 are included in the visual display 400.

The visual display 400 can include physiology fields 424. The physiology fields 424 are provided adjacent the markers 422. In the embodiment of FIG. 4, only a portion of the physiology fields 424 are shown. In various embodiments, a portion, all, or none of the physiology fields 424 can provide the computed physiology quantity associated with a given location. For example, a user can selectively activate or deactivate one or more of the physiology fields 424. In various embodiments, the physiology fields 424 include alphabetical, numerical, alphanumeric, and/or symbolic characters. In FIG. 4, the fields 424 include numeric values associated with a pressure ratio calculation. In other embodiments, the fields 424 can include an "FFR," "iFR," "Pd/Pa," "CFR," "Temp," or other label to identify the type of quantity being displayed. Such embodiments are described, for example, in U.S. Provisional Application No. 61/895,909, titled "Devices, Systems, and Methods for Vessel Assessment," and filed Oct. 25, 2013, the entirety of which is hereby incorporated by reference herein.

The visual display 400 can include various colors, patterns, and/or other visual indicators 426 representative of the physiology data. For example, the indicators 426 can be representative of a difference between a threshold pressure ratio and the actual pressure ratio. For example, a first color (e.g., green, white, or otherwise) can be utilized to represent values well above the threshold value (e.g., where the threshold value is 0.80 on a scale of 0.00 to 1.00, values above 0.90), a second color (e.g., yellow, gray, or otherwise) can be utilized to represent values near but above the threshold value (e.g., where the threshold value is 0.80 on a scale of 0.00 to 1.00, values between 0.81 and 0.90), and a third color (e.g., red, black, or otherwise) can be utilized to represent values equal to or below the threshold value (e.g., where the threshold value is 0.80 on a scale of 0.00 to 1.00, values of 0.80 and below). It is appreciated that any number of color combinations, scalings, categories, and/or other characteristics can be utilized to visually represent the relative value of the pressure differential to the threshold value. However, for the sake of brevity Applicants will not explicitly describe the numerous variations herein. The severity key or index 430 shows the colors 432 and their corresponding physiological values 434.

The visual display 400 can include visual indicator 456 associated with an automatically determined location of a lesion. The computing device 110 can automatically identify and classify the type of lesion as described in, for example, U.S. Provisional Application No. 62/089,090, "AUTOMATED IDENTIFICATION AND CLASSIFICATION OF INTRAVASCULAR LESIONS" filed Dec. 8, 2014, the entirety of which is hereby incorporated by reference herein. Because the indicators 422 and 440 identify the location of the physiology data and intravascular imaging data, the clinician can easily evaluate the vasculature surrounding the indicator 456.

The visual display 400 also includes markers 440 indicative of a location within the vessel 414 associated with the collected intravascular imaging data. For example, the markers 400 can be a location of the IVUS or OCT component when the intravascular images were acquired. In the embodiment of FIGS. 4 and 7, the markers 440 are line segments that transect the vessel 414. In the embodiment of FIGS. 5 and 6, the markers 440 are symbols positioned along or within the vessel 414. While a diamond is shown in FIGS. 5 and 6, it is understood that any suitable shape or symbol can be used. In some embodiments, a user can selectively activate or deactivate one or more of the markers 440 such that a portion, all, or none of the markers 440 are included in the visual display 400.

The visual components illustrated in FIG. 4 can be variously displayed by the display device 150. For example, a holographic display device can display the heart 412, the vessel 414, 416, and the visual indicators associated therewith in a three-dimensional manner. The severity key or index 430, control options 470, and/or the supplemental display 480 can be displayed in a two-dimensional manner. In that regard, the two-dimensional components can be output by the same display device, such as the holographic display device, as the three-dimensional components. For example, the two-dimensional components can be display alongside the three-dimensional components. In other embodiments, different portions of the same display device or different display devices can output the two-dimensional and three-dimensional components. For example, a holographic display device can include a portion configured to output the heart 412, and the vessels 414 and 416 in a three-dimensional manner, and a portion configured output the severity key or index 430, control options 470, and/or the supplemental display 480 in a two-dimensional manner. In other embodiments, the display device 150 is a monitor or touch screen display device. Two-dimensional images and/or two-dimensional representations of the three-dimensional models associated with the heart 412, and the vessels 414 and 416 can be displayed. The severity key or index 430, control options 470, and/or the supplemental display 480 can also be displayed by the monitor or touch screen display device.

The visual display 400 includes control options 470, such as pan controls 472, zoom controls 474, and rotate controls 476. The three-dimensional graphical representation can be displayed in the desired orientation, position, and/or magnification based the user input. In some embodiments, the pan controls 472, the zoom controls 474, and the rotate controls 476 are selectable options in the visual display 400 (e.g., selected based on a user touch input on a touch-sensitive display). In some embodiments, the pan controls 472, the zoom controls 474, and the rotate controls 476 are not expressly provided, but the clinician provides user touch inputs that the computing device 110 correlates to the desired modification of the graphical representation. In other embodiments, in lieu of or in addition to the pan controls 472, the zoom controls 474, and the rotate controls 476, a clinician can use hand gestures (e.g., hand or fingers swiping from side to side to pan, hand or fingers twisting to rotate, pinching with hands or finders to zoom, etc.) to display the graphical representation the desired orientation, position, and/or magnification.

The visual display 400 includes a measure field 478. In some embodiments, selecting the measure field can allow a clinician to measure one or more dimensions on the graphical representation of the heart or vessel, such as the length and/or diameter of an occlusion and/or the diameter of a vessel at the shoulders of the lesion. In some embodiments, the measure field is not expressly provided, but the clinician provides user touch inputs (e.g., drawing a line or circle, etc.) that the computing device 110 correlates to the desired modification of the graphical representation. In other embodiments, in lieu of or in addition to the measure field, a clinician can use hand gestures (e.g., drawing a line or circle, etc.) to measure the one or more dimensions of the anatomy. The computing device 110 can utilize the external imaging data, intravascular imaging data, physiologic data, and/or cardiac test data to correlate a dimension in the graphical representation to an actual, anatomical value. The visual display 400 can include a measurement indicator 462 that illustrates the dimension that is measured. The visual display 400 can also include the measurement value 464 that provides the numerical value associated with the measurement.

The visual display 400 includes the supplemental display 480. The supplemental display 480 includes one or more field providing additional graphical representations, such as the obtained physiology data, external imaging data, intravascular imaging data, and/or cardiac test data. For example, selecting one of the indicators 422 and/or 440 can provide the associated physiology data in the physiology field 482 and/or the associated intravascular imaging data in the imaging field 484. In FIG. 4, the indicators 422 and 440 that are surrounded by the selection fields 452 and 454 are selected. The physiology value (the FFR value in the illustrated embodiment) and the intravascular image (e.g., the IVUS image in the illustrated embodiment) are provided in the physiology field 482 and imaging field 484. FIG. 8 illustrates the supplemental display 480 including the cardiac test field 486. In the illustrated embodiment, myocardial perfusion images acquired by a SPECT camera are provided.

Referring again to FIG. 4, by providing the indicators 422 and 440 in the visual display 400, the clinician can make more accurate measurements of the lesion length and/or lumen diameter. The lesion length and/or lumen diameter are in turn used to select the stent length and diameter during PCI planning. For example, indicators 440, which are associated with intravascular images, at the proximal end and distal end of a lesion can be selected. By viewing the intravascular images, the shoulders of the lesion can be accurately identified. The clinician can then measure a length from the proximal shoulder to the distal shoulder to determine a length of the stent. Similarly, the measured diameter of the lumen at the proximal shoulder or distal shoulder can be used to select the diameter for the stent. The stent length can also be selected to span a pressure drop caused by a lesion, as indicated by the physiology data.

Referring to FIG. 5, shown therein is a visual display 500 including a three-dimensional graphical representation 510 of a vessel. The graphical representation 510 includes the vessel 414 from the graphical representation 410 (FIG. 4). The three-dimensional graphical representation of the vessel can be generated based on the obtained external imaging data and the intravascular imaging data. For example, the three-dimensional model of the vessel 414 can include the position, contours, and other characteristics of the lesion 502. The visual display 500 can be outputted by the display device 150 in response to a user input to view the particular vessel in isolation (e.g., apart from surrounding anatomy, such as the heart). The clinician can switch between the visual display 400 including the graphical representations of the vessel 414 and the heart 412 and the visual display 500 including only the vessel 414. Viewing the visual display 500 (as opposed to the visual display 400) can facilitate PCI planning when the lesion 502 is known to be present in the vessel 414. For example, the clinician can more easily select the indicators 422 and 440 around the lesion 502 to view the associated physiology data and/or intravascular imaging data. The clinician can also more easily measure the dimensions associated with the vessel 414 to determine the parameters for the stent. The indicators 422 and 440 can be provided at various positions along the vessel 414 corresponding to the path the pressure transducer and/or imaging component through the vessel 414. For example, the pressure transducer and/or imaging component can be closer or farther from the lumen border of the vessel 414.

Referring to FIG. 6, shown therein is a visual display 600 including a three-dimensional graphical representation 610 of a vessel cross-section. FIG. 6 illustrates a vertical cross-section of the vessel 414. In other embodiments, the computing device 110 can generate display data associated the horizontal cross-section of the vessel 414. The graphical representation 610 includes the vessel 414 from the graphical representation 410 (FIG. 4) and graphical representation 410 (FIG. 5). The three-dimensional, cross-sectional graphical representation of the vessel can be generated based on the obtained external imaging data and the intravascular imaging data. For example, the three-dimensional, cross-sectional model of the vessel 414 can include the position, contours, plaque structure, plaque composition, and other characteristics of the lesion 502, including the plaque components 602 and 604. Viewing the visual display 600 can facilitate PCI planning. For example, the clinician can more easily select the indicators 422 and 440 around the lesion 502 to view the associated physiology data and/or intravascular imaging data. The clinician can also more easily measure the dimensions associated with the vessel 414, such as the length of the length of the lesion and/or the lumen diameter, to determine the parameters for the stent. The indicators 422 and 440 can be provided at various positions along the vessel 414 corresponding to the path the pressure transducer and/or imaging component through the vessel 414. For example, the pressure transducer and/or imaging component can be closer or farther from the lumen border of the vessel 414.

Referring to FIG. 7, shown therein is a visual display 700 including a three-dimensional graphical representation 710 of the heart including a graphical representation of the cardiac test data. The graphical representation of the cardiac test data can be generated based on the external imaging data and/or the cardiac test data. Exemplary myocardial perfusion imaging data is illustrated in FIG. 8. The graphical representation 710 includes the heart 412 including coloration, shading, pattern, or other suitable visual indicator representative of blood flow to the myocardium or heart muscle. The indicator can be gradated to illustrate differing amounts of blood flow to and/or oxygenation of the heart muscle. For example, the region 702 can be representative of normal, healthy blood flow/oxygenation. The region 704, which in the illustrated embodiment is visualized with a darker coloration, can be representative of less than normal blood flow/oxygenation. The region 706, which is visualized with an even darker coloration, can be representative of damaged heart tissue with very poor blood flow/oxygenation. Various schemes for gradated coloration, pattern, and/or shading can be used in different embodiments. The region 704 can be the result of an occlusion in the vessel 414. The region 706 can be representative of damaged tissue resulting from the patient's previous heart attacks.

The control options 470 can include an insert stent field 479. Selection of the insert stent field 479 can be a user input to modify the visual representation 710 to insert a graphical representation of the stent in, e.g., the graphical representation of the vessel 414. As illustrated in FIG. 9, the graphical representation of the vessel 414 includes stents 710 and 712. The parameters of the stent (e.g., the length, diameter, position) can be automatically determined by the computing device 110 or manually input by the clinician. The computing device 110 can determine the simulated physiologic effects of a stent of a given length and diameter, at a given position, being deployed in the vessel. For example, based on the association between the vessel 414 and the heart tissue, deployment of the stents 710 and/or 712 can cause the region 704 to have normal blood flow/oxygenation. The region 706, however, does not return to normal blood flow/oxygenation because the tissue is damaged from a patient's previous occlusions. The graphical representation of the simulated physiologic effects can be modified based on the parameters of the stents 710 and 712. Thus, the clinician can conduct PCI planning using the visual display 900 by optimizing the length, diameter, and/or position of the stents 710 and 712 to return the myocardium to as normal blood flow/oxygenation as possible. The supplemental display 480 of FIGS. 7 and 9 can provide physiology data or quantities, intravascular imaging data, and/or cardiac test data, as shown FIGS. 4-6 and 8. As described herein, the physiology data or quantities and/or intravascular imaging data can be provided in response to a user input to select an indicator associated with the location of the physiology data and/or intravascular imaging data. For example, the cardiac test data can be provided in response to a user input select a portion of the graphical representation of heart 412. The cardiac test data, such as SPECT data, corresponding to the selected area of the heart can be displayed in the supplemental display 480.

In some embodiments, the visual representations of the physiology data, intravascular imaging data, and/or cardiac test data provided on the three-dimensional graphical representation of the heart and/or vessel can be associated with one or more layers that can be selectively displayed. For example, indicators 422, the physiology fields 424, and/or indicators 426 can be a part of a physiology data layer. The indicators 440 can be part of the intravascular imaging layer. The regions 702, 704, and 706 can be part of a cardiac test data layer. The visual representations associated with each layer can shown/hidden in response to a user input, e.g., received at the input device 160. Further, the particular visual representations included in each layer, as well as their characteristics, can be selected by a user input.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for evaluating a vascular system of a patient, the system comprising:
 a guide wire or catheter sized and shaped for introduction into a vessel of a heart and comprising a sensor configured to obtain physiology data associated with blood flow through the vessel; and a processor communicatively coupled to the guide wire or catheter, a memory, and a display device, the processor operable to execute instructions stored in the memory to:
receive external imaging data representative of the vessel, wherein the external imaging data comprises three-dimensional information of the vessel;
receive myocardial perfusion imaging data associated with the blood flow to a myocardium of the heart via the vessel, wherein the myocardial perfusion imaging data comprises three-dimensional information of the myocardium;
receive the physiology data associated with the blood flow through the vessel from the sensor of the guide wire or catheter;
generate a three-dimensional model using the external imaging data, the myocardial perfusion imaging data, and the physiology data, wherein the three-dimensional model comprises the vessel and a region of the myocardium associated with the vessel;
identify, using the three-dimensional model, a stenosis of the vessel restricting the blood flow to the region of the myocardium;
identify, using the three-dimensional model, a location of the region of the myocardium and the blood flow to the region of the myocardium;
generate a three-dimensional graphical representation of the three-dimensional model;
output the graphical representation to the display device, wherein the graphical representation includes a graphical representation of the myocardial perfusion imaging data having a first visual characteristic at the location of the region of the myocardium;
determine, using the three-dimensional model, a simulated effect of a therapeutic intervention on the stenosis, the simulated effect comprising an increase in the blood flow to the region of the myocardium; and
output a modified three-dimensional graphical representation, the modified graphical representation including a graphical representation of the simulated effect comprising a second visual characteristic at the location of the region of the myocardium, the second visual characteristic different than the first visual characteristic.

2. The system of claim 1, wherein the processor executing the instructions to receive the external imaging data includes the processor executing instructions to receive at least one of angiography data or computed tomography data.

3. The system of claim 1, wherein the display device includes at least one of a touch-sensitive display device or a holographic display device.

4. The system of claim 1,
wherein the processor executing the instructions to output the graphical representation includes the processor executing instructions to output the first visual characteristic comprising at least one of a pattern, shading, or coloration representative of the blood flow to the myocardium, and
wherein the processor executing the instructions to output the modified graphical representation includes the processor executing instructions to output the second visual characteristic comprising at least one of a different pattern, a different shading, or a different coloration.

5. The system of claim 1, wherein the processor executing the instructions to receive the physiology data associated with the vessel includes the processor executing instructions to receive at least one of pressure measurements, flow measurements, or temperature measurements.

6. The system of claim 1, further comprising:
an input device communicatively coupled to the processor, wherein the input device is configured to receive a user input to simulate the therapeutic intervention.

7. The system of claim 1, wherein the processor executing the instructions to determine the simulated effect of the therapeutic intervention includes the processor executing instructions to determine the simulated effect of a percutaneous coronary intervention.

8. The system of claim 6, wherein the input device receiving the user input includes at least one of:
receiving a user touch input, when the input device comprises a touch-sensitive display device, or
acquiring a hand gesture.

9. The system of claim 1, wherein the processor executing the instructions to output the graphical representation includes the processor executing instructions to output the graphical representation comprising an indicator representative of a location of the vessel associated with the physiology data.

10. The system of claim 1, further comprising:
an intravascular imaging sensor communicatively coupled to the processor,
wherein the processor is further operable to execute instructions to:
receive, from the intravascular imaging sensor, intravascular imaging data associated with the vessel, and
generate the graphical representation using the external imaging data and the intravascular imaging data.

11. The system of claim 10, wherein the processor executing the instructions to output the graphical representation includes the processor executing instructions to output the graphical representation comprising an indicator representative of a location of the vessel associated with the intravascular imaging data.

* * * * *